(12) United States Patent
Gadrat et al.

(10) Patent No.: US 11,607,478 B2
(45) Date of Patent: *Mar. 21, 2023

(54) SYSTEM AND METHOD FOR TREATING HAEMORRHAGIC FLUID FOR AUTOTRANSFUSION

(71) Applicant: I-SEP, Nantes (FR)

(72) Inventors: Francis Gadrat, Bordeaux (FR); Stéphane Chollet, La Chapelle sur Erdre (FR); Sylvain Picot, Caluire et Cuire (FR); Patricia Forest-Villegas, Genas (FR)

(73) Assignee: I-SEP

( * ) Notice: Subject to any disclaimer, the term of this patent is extended or adjusted under 35 U.S.C. 154(b) by 358 days.

This patent is subject to a terminal disclaimer.

(21) Appl. No.: 16/958,458

(22) PCT Filed: Dec. 21, 2018

(86) PCT No.: PCT/FR2018/053501
§ 371 (c)(1),
(2) Date: Jun. 26, 2020

(87) PCT Pub. No.: WO2019/129974
PCT Pub. Date: Jul. 4, 2019

(65) Prior Publication Data
US 2021/0052789 A1    Feb. 25, 2021

(30) Foreign Application Priority Data

Dec. 28, 2017   (FR) ........................ 1763308
Dec. 28, 2017   (FR) ........................ 1763310

(51) Int. Cl.
*A61M 1/02*    (2006.01)
*A61M 1/36*    (2006.01)
*A61M 1/38*    (2006.01)

(52) U.S. Cl.
CPC ........ *A61M 1/0281* (2013.01); *A61M 1/0218* (2014.02); *A61M 1/3603* (2014.02);
(Continued)

(58) Field of Classification Search
CPC .............. A61M 1/0281; A61M 1/0218; A61M 1/3603; A61M 1/38; A61M 2205/3306;
(Continued)

(56) References Cited

U.S. PATENT DOCUMENTS

| 4,886,487 A | 12/1989 | Solem et al. |
| 5,215,519 A | 6/1993 | Shettigar |

(Continued)

FOREIGN PATENT DOCUMENTS

| EP | 0341413 A2 | 11/1989 |
| EP | 0400518 A2 | 12/1990 |

(Continued)

OTHER PUBLICATIONS

French Preliminary Search Report for Application No. 1763308 completed Aug. 2, 2018, 2 pages.

(Continued)

*Primary Examiner* — John Kim
(74) *Attorney, Agent, or Firm* — Lerner, David, Littenberg, Krumholz & Mentlik, LLP

(57) ABSTRACT

The invention relates to a system, and the associated method for using said system, for treating haemorrhagic fluid previously taken from a patient for the purpose of autotransfusion, comprising a unit for treating (100) haemorrhagic fluid, said treatment unit (100) comprising:
 a filtration device (110) for tangential filtration comprising a filtration membrane (113) arranged in a housing (114) so as to separate an intake chamber (111) from a discharge chamber (112), the intake chamber (111) and
(Continued)

the discharge chamber (112) each having an inlet (111a; 112a) and an outlet (111b; 112b) for fluids;

a treatment pouch (140) having an inlet (140a) and an outlet (140b) fluidically connected by a recirculation line (150) to the outlet (111b) and to the inlet (111a) of the intake chamber (111) of the filtration device (110), respectively, allowing haemorrhagic fluid to circulate in the recirculation line (150) in a direction going from the outlet (140b) of the treatment pouch (140) to the inlet (140a) of the treatment pouch (140) through the intake chamber (111) of the filtration device (110);

a cleaning line (180) fluidically connected to the inlet (112a) of the discharge chamber (112) of the filtration device (110) to convey cleaning fluid into said discharge chamber (112); and a first flow regulation member (181) arranged to regulate the flow in the cleaning line (180) and a second flow regulation member (131) arranged to regulate the flow in a discharge line (130) fluidically connected to the outlet (112b) of the discharge chamber (112) of the filtration device (110), so as to be able to control the pressure of cleaning fluid in the discharge chamber (112).

27 Claims, 6 Drawing Sheets

(52) U.S. Cl.
CPC ....... *A61M 1/38* (2013.01); *A61M 2205/3306* (2013.01); *A61M 2205/3331* (2013.01); *A61M 2205/3334* (2013.01); *A61M 2205/581* (2013.01); *A61M 2205/582* (2013.01); *A61M 2205/583* (2013.01); *A61M 2205/7554* (2013.01)

(58) Field of Classification Search
CPC .. A61M 2205/3331; A61M 2205/3334; A61M 2205/581; A61M 2205/582; A61M 2205/583; A61M 2205/7554
See application file for complete search history.

(56) References Cited

U.S. PATENT DOCUMENTS

| | | |
|---|---|---|
| 5,298,016 A | 3/1994 | Gordon |
| 5,858,238 A | 1/1999 | McRea et al. |
| 6,251,295 B1 | 6/2001 | Johnson |
| 6,994,781 B2 | 2/2006 | Cork et al. |
| 7,686,777 B2 | 3/2010 | Huang et al. |
| 7,722,557 B2 | 5/2010 | Sano et al. |
| 8,257,590 B2 | 9/2012 | Taniguchi et al. |
| 8,388,847 B2 | 3/2013 | Mitterer et al. |
| 8,569,052 B2 | 10/2013 | Federspiel et al. |
| 8,758,603 B2 | 6/2014 | Okazaki |
| 9,341,626 B2 | 5/2016 | Humes et al. |
| 9,446,074 B2 | 9/2016 | Kishikawa et al. |
| 2003/0138349 A1 | 7/2003 | Robinson et al. |
| 2003/0229302 A1 | 12/2003 | Robinson et al. |
| 2006/0081524 A1 | 4/2006 | Sengupta et al. |
| 2007/0163942 A1 | 7/2007 | Tanaka et al. |
| 2012/0226258 A1 | 9/2012 | Otto et al. |
| 2014/0287502 A1 | 9/2014 | Taniguchi |
| 2015/0306295 A1 | 10/2015 | Rovatti |
| 2015/0314057 A1 | 11/2015 | Labib et al. |
| 2016/0074569 A1 | 3/2016 | Schuetz et al. |
| 2016/0096148 A1 | 4/2016 | Schuetz et al. |
| 2016/0158425 A1 | 6/2016 | Cotton et al. |
| 2016/0158670 A1 | 6/2016 | Tanizaki et al. |
| 2016/0168529 A1 | 6/2016 | Taniguchi et al. |
| 2016/0317972 A1 | 11/2016 | Matsumoto et al. |
| 2016/0339159 A1 | 11/2016 | Nosaka et al. |

FOREIGN PATENT DOCUMENTS

| | | |
|---|---|---|
| EP | 2461847 A1 | 6/2012 |
| EP | 2631645 A1 | 8/2013 |
| EP | 2735326 A1 | 5/2014 |
| EP | 2735360 A1 | 5/2014 |
| WO | 199301858 A1 | 2/1993 |
| WO | 199829149 A1 | 7/1998 |
| WO | 2019129974 A1 | 7/2019 |

OTHER PUBLICATIONS

French Preliminary Search Report for Application No. 1763310 completed Apr. 2, 2018, 2 pages.
Fukunaga, et al., "In Vitro Evaluation Study of the Membrane Autotransfusion System Experimental Prototype: MATS-I," Artificial Organs. Feb. 1, 2000, pp. 95-102, vol. 24, No. 2.
Fukunaga, et al., Preliminary evaluation study of a prototype hollow fiber membrane for the continuous membrane autotransfusion system. Therapeutic Apheresis. Feb. 3, 1999, pp. 63-68, vol. 3, No. 1.
International Search Report for Application No. PCT/FR2018/053500 dated Apr. 10, 2019, 2 pages.
International Search Report for Application No. PCT/FR2018/053501 dated Mar. 7, 2019, 2 pages.
French Preliminary Search Report for Application No. 1907004 dated May 13, 2020, 3 pages. [see p. 3, categorizing the cited references].
Gadrat, F. et al., U.S. Appl. No. 16/958,473, filed Jun. 26, 2020, titled "System And Method For Treating Haemorrhagic Fluid For Autotransfusion".
International Search Report for Application No. PCT/FR2020/051115 dated Oct. 7, 2020, 3 pages.
Search Report dated Oct. 11, 22 from Office Action for Chinese Application No. 201880090348.0 dated Oct. 24, 2022. 3 pgs.

SYSTEM AND METHOD FOR TREATING HAEMORRHAGIC FLUID FOR AUTOTRANSFUSION

CROSS-REFERENCE TO RELATED APPLICATIONS

The present application is a national phase entry under 35 U.S.C § 371 of International Application No. PCT/FR2018/053501 filed Dec. 21, 2018, which claims priority from French Application Nos. 1763308 and 1763310 both filed Dec. 28, 2017, all of which are hereby incorporated herein by reference.

FIELD OF THE INVENTION

The present invention relates to the field of treatment of haemorrhagic fluid such as blood to carry out an autotransfusion on a patient, notably during a surgical intervention.

PRIOR ART

Autotransfusion or autologous transfusion, namely the transfusion in a patient of the patient's own blood, is increasingly practised during surgical interventions since it avoids the incompatibilities that can exist with homologous or allogenic transfusions, that is to say transfusions from the blood of another person, and it notably prevents the transmission of infectious diseases.

In the case of intraoperative autotransfusion, it is important to be able to transfuse the blood collected directly from the patient almost continuously that is to say while limiting the dead time due notably to the treatment of the blood, this treatment being carried out with a treatment device independently of the patient. Yet, during collection, in a known manner, anticoagulant agents must also be added to this blood already diluted by the operating conditions to enable treatment by an autotransfusion device and to preserve its transfusional quality and the functionalities of the blood elements. These actions appear necessary because by using a vector fluid for the collected haemorrhagic blood, the red blood cells may thus be protected from direct physical traumatisms during mechanical contact with the filters and other tubing. This dilution in a fluid vector also decreases contact of the red blood cells with air, thus greatly limiting their haemolysis. Finally, it also makes it possible to control and prevent the coagulating activity of the blood and to avoid the formation of clots which would not enable the recovery of blood elements, notably red blood cells. The recovered blood must next be transfused to the patient in order to compensate the loss of blood volume, but this raises important problems. Indeed, in the case of transfusion of too diluted blood volumes, it is possible to cause hypervolemia phenomena by these too important transfused fluid volumes and hypocoagulability syndromes for the same reasons and/or by a too important transfused volume of anticoagulant if not cleaned.

In addition, during autotransfusion of blood taken directly and only anticoagulated and haemodiluted, it is possible to transfuse activated or degraded biological substances liable to cause secondary effects. It is possible to find for example histamines, kallikreins or kinins, plasmatic factors more or less degraded which it is better to get rid of or instead small proteins and other cellular debris originating from cellular traumatisms.

For intraoperative autotransfusion conditions, the treatment of the blood thus consists in collecting the blood, anticoagulating it (which leads to dilution) simultaneously on taking the blood, then prefiltering it in the prefiltration jar and treating it by the treatment device so as to separate the fluid phase from the phase containing the cellular elements thus enabling on the one hand a concentration of the collected phase intended to be transfused and on the other hand a collection of the fluid phase to eliminate. It should be specified that these steps must be carried out as quickly as possible since the patient, in intraoperative conditions, generally needs to be transfused urgently.

Different techniques, more or less complex and efficient for carrying out autotransfusion on a patient during surgical interventions, have been developed.

Autotransfusion systems based on centrifugation techniques exist for example. Centrifugation of the blood taken in autotransfusion ensures the separation of red blood cells (RBC) and plasma containing platelets (PRP) and proteins. A high platelet recovery level is thus impossible by this method.

Further, for the process to be rapid, a stronger centrifugation may be carried out but a layer is then going to form at the interface between the red blood cells and the plasma, which is called buffy coat, which is a mixture of platelets and white blood cells (WBC). This layer is thus unfit for direct transfusion.

It is thus necessary to apply complementary treatments to recover the platelets and to eliminate undesired elements such as the buffy coat. Further, when the centrifugation is too strong, there is going to be elimination of platelets and thus an impoverishment of the quality of the concentrate to transfuse.

The taking of blood and biological fluids by the surgeon by suction induces traumatism of the red blood cells leading to mechanical haemolysis of the most fragile cells. Centrifugation, a mechanism known and widely used in autotransfusion, also leads to slight mechanical haemolysis. During the intraoperative treatment of blood by centrifugation, the red globules thus undergo traumatisms leading to important haemolysis, which can go up to 19%. In emergency mode (stronger centrifugation to decrease the treatment time), this haemolysis rate may go up to 33%.

An alternative to current methods for intraoperative treatment of blood by centrifugation is desired because centrifugation, apart from the problems of haemolysis, eliminates the majority of the platelets (recovery rate less than 10%). This direct loss of cells of interest, participating directly in primary haemostasis (platelet aggregation at the level of the wound), is problematic during an operation as may easily be understood. Which is why, when the losses are too considerable, physicians can resort to the transfusion of labile blood products of which one or more homologous platelet concentrates. A method that would make it possible to conserve and transfuse the platelets (with preferably a recovery rate greater than 50%) of the patient would be consequently appreciable.

Alternative autotransfusion systems have thus been developed, based on membrane filtration devices. This is for example the case of the autotransfusion systems described in the U.S. Pat. No. 4,886,487, in the U.S. Pat. No. 5,215,519 and in the patent application US 2003/229302. These systems are advantageous in the sense that they enable actual separation of undesired elements for the blood transfusion, without eliminating important elements such as platelets as is the case during centrifugation. Such systems have however a certain number of drawbacks, notably in terms of efficiency.

The cells (RBC, WBC and platelets) have high membranal deformability making it possible for them to pass through blood micro-vessels or wounds. However, during filtration on a membrane, a drop in the filtration flow is observed throughout the process. The drop off in the flow may be explained by several factors, namely, adsorption, steric hindrance, viscosity effects, obstruction and clogging of the pores, as well as the concentration gradient at the membrane/solution interface.

In the case of filtration, the size of the pores and the hydrophilicity of the materials must be controlled in order to allow these cells to pass through or not. In the case of use of a membrane with pores of diameters less than 10 µm, in particular less than 1 µm, the clogging of the membranes by the cells is obligatory in frontal filtration, hence the necessity of tangential filtration. The platelets also have high adhesiveness after activation and have a tendency to be adsorbed on the surface of the membranes or to plasmatic proteins and clog the membranes.

Tangential filtration is subject to the quantity of material being able to pass through the membrane per time unit, which in general limits the treatment speed. Transmembrane flow rate or filtration coefficient are spoken of. However, a patient suffering from a massive haemorrhage cannot see his loss of chance coefficient increase on account of a longer filtration time. It is thus vital that the intraoperative time for treating the blood by filtration is comparable to the conventional centrifugation method, where separation of red blood cells and plasma may be done in a rapid time of 4-6 minutes for a volume of collected blood of 500 ml.

In the same way as for the treatment time, the performances of the treatment by membrane filtration must be at least comparable to intraoperative treatment of blood by the centrifugation method (red blood cell recovery rate greater than 80%, quantity of heparin less than 0.5 IU/ml).

There exists today a need for an improved system for treating blood for autotransfusion, notably making it possible to resolve at least one of the aforesaid drawbacks.

An aim of the present invention is also to propose a system for treating blood for autotransfusion that is easy to use and intuitive, so as to be able to be used by professionals with little or no training.

DESCRIPTION OF THE INVENTION

For this purpose, a system is proposed for treating a haemorrhagic fluid previously taken from a patient for the purpose of autotransfusion, comprising a unit for treating haemorrhagic fluid, said treatment unit comprising:
  a filtration device for tangential filtration comprising a filtration membrane arranged in a housing so as to separate an intake chamber from a discharge chamber, the intake chamber and the discharge chamber each having an inlet and an outlet for fluids;
  a treatment pouch having an inlet and an outlet fluidically connected by a recirculation line to the outlet and to the inlet of the intake chamber of the filtration device, respectively, allowing haemorrhagic fluid to circulate in the recirculation line in a direction going from the outlet of the treatment pouch to the inlet of the treatment pouch through the intake chamber of the filtration device;
  an intake line fluidically connected to the recirculation line between the outlet of the treatment pouch and the inlet of the intake chamber of the filtration device making it possible to supply the treatment unit with haemorrhagic fluid taken for the purpose of filtration through the filtration membrane of the filtration device in order to remove from the haemorrhagic fluid a filtrate comprising compounds undesired for autotransfusion;
  a transfusion line fluidically connected to the recirculation line between the outlet of the treatment pouch and the inlet of the intake chamber of the filtration device making it possible to recover treated haemorrhagic fluid contained in said treatment pouch;
  a discharge line fluidically connected to the outlet of the discharge chamber of the filtration device so as to discharge the filtrate having traversed the filtration membrane from the intake chamber;
characterised in that the treatment unit further comprises
  a cleaning line fluidically connected to the inlet of the discharge chamber of the filtration device to convey cleaning fluid into said discharge chamber; and
  a first flow regulation member arranged to regulate the flow in the cleaning line and a second flow regulation member arranged to regulate the flow in the discharge line so as to be able to control the pressure of cleaning fluid in the discharge chamber.

Preferred but non-limiting aspects of this treatment system, taken alone or in combination, are the following:
  the cleaning line is further fluidically connected to the recirculation line at a first position between the outlet of the treatment pouch and the inlet of the intake chamber of the filtration device, the treatment unit further comprising a dilution line intended to convey a dilution fluid into the treatment unit, the dilution line being fluidically connected to the recirculation line at a second position between the outlet of the treatment pouch and the inlet of the intake chamber of the filtration device, the dilution fluid being able to be used as cleaning fluid.
  the treatment unit comprises a third flow regulation member arranged to regulate the flow in the dilution line, a fourth flow regulation member arranged to regulate the flow in the recirculation line at the outlet of the treatment pouch, and a fifth flow regulation member arranged to regulate the flow in the recirculation line at the inlet of the intake chamber of the filtration device.
  the second position is situated upstream of the first position in the direction of circulation of the fluid in the recirculation line during the treatment of haemorrhagic fluid.
  the system comprises a single peristaltic pump arranged so as to make haemorrhagic fluid circulate in the recirculation line in a direction going from the outlet of the treatment pouch to the inlet of the treatment pouch through the intake chamber of the filtration device, said peristaltic pump being positioned in the recirculation line between the outlet of the treatment pouch and the inlet of the intake chamber of the filtration device between the second position and the first position.
  the system comprises at least one peristaltic pump arranged so as to make haemorrhagic fluid circulate in the recirculation line in a direction going from the outlet of the treatment pouch to the inlet of the treatment pouch through the intake chamber of the filtration device.
  the treatment pouch comprises a separating device being able to be actuated to separate the treatment pouch into a first treatment chamber on the side of the inlet of the treatment pouch and a second treatment chamber on the side of the outlet of the treatment pouch.

the treatment pouch has a substantially parallelepiped shape with the inlet and the outlet on either side of the treatment pouch along a diagonal, the treatment pouch further having an inner cavity having a tapering shape on the outlet side.

the filtration membrane of the filtration device is a filtration membrane with hollow fibres, said hollow fibres forming the filtration membrane extending longitudinally in the housing.

the filtration membrane with hollow fibres of the filtration device comprises hollow fibres formed from a mixture of polyester sulfone and polyvinyl pyrrolidone.

the filtration membrane of the filtration device has an overall porosity comprised between 0.1 µm and 1 µm, preferably of the order of 0.6 µm.

the filtration membrane of the filtration device has an overall filtration surface area comprised between 0.1 m$^2$ and 1 m$^2$, and preferably comprised between 0.2 m$^2$ and 0.6 m$^2$.

the treatment unit comprises a sixth flow regulation member arranged to regulate the flow in the transfusion line.

the treatment system comprises a plurality of regulation valves, each regulation valve being respectively intended to cooperate with one of the regulation members in order to regulate the corresponding flow.

the treatment unit comprises a template enabling fixation of the intake line, the discharge line, the recirculation line, the transfusion line and the cleaning line.

the treatment system comprises a support unit, the template of the treatment unit having a mistake-proofing shape making it possible to couple the treatment unit to the support unit according to a unique positioning, preferably removably.

the support unit forms a horizontal support plane, the filtration device of the treatment unit being intended to be coupled to the support unit such that the hollow fibres of the filtration membrane extend along a direction not comprised in the horizontal support plane.

the treatment system comprises a transfusion unit, said transfusion unit comprising a transfusion pouch having an inlet intended to be connected to the transfusion line in order to collect treated haemorrhagic fluid coming from the treatment pouch before transfusion to the patient.

the treatment system comprises a filtrate recovery unit, said recovery unit comprising a recovery pouch having an inlet intended to be fluidically connected to the discharge line, said recovery pouch being further intended to be coupled to a device for depressurising the recovery pouch so as to make the filtrate circulate from the discharge chamber of the filtration device to the recovery pouch through the discharge line.

the treatment system comprises a filtrate recovery unit, said recovery unit comprising a recovery pouch having an inlet intended to be fluidically connected to the discharge line, said recovery pouch being further arranged with respect to the filtration device of the treatment unit to create a vacuum pressure in the recovery pouch with respect to the filtration device so as to make the filtrate circulate from the discharge chamber of the filtration device to the recovery pouch through the discharge line.

the treatment system comprises a unit for collecting haemorrhagic fluid comprising a receptacle for collecting haemorrhagic fluid previously taken from the patient, said collection receptacle having an outlet fluidically connected to the intake line, said collection receptacle preferably integrating a prefiltration device making it possible to carry out prefiltration of haemorrhagic fluid before being transmitted into the treatment unit.

the treatment system further comprises an additional prefiltration device placed in the intake line.

A method is also proposed for using this system for treating haemorrhagic fluid previously taken from a patient for the purpose of later autotransfusion wherein, after partial or total treatment of haemorrhagic fluid with the filtration device, cleaning of the filtration membrane is carried out while creating a transmembrane counterflow, the counterflow being created by obstructing the discharge line at the level of the second flow regulation member and by injecting cleaning fluid into the discharge chamber from the cleaning line, the pressure created in the discharge chamber by the injection of the cleaning fluid creating a counterflow through the filtration membrane making it possible to remove all or part of the elements retained on the filtration membrane.

Preferred but non-limiting aspects of this method for using the treatment system, taken alone or in combination, are the following:

counterflow cleaning is carried out at regular intervals during the treatment of a determined volume of haemorrhagic fluid.

counterflow cleaning is carried out after the total treatment of a determined volume of haemorrhagic fluid.

counterflow cleaning is carried out by varying the speed of circulation of the cleaning fluid, in particular by increasing and decreasing said speed of circulation of the cleaning fluid.

a determined volume of haemorrhagic fluid coming from the intake line is treated by making it circulate in the circulation line in order to pass through the filtration device several times to remove compounds undesired for autotransfusion, the treatment pouch making it possible to maintain a flow having a continuous flow rate in the circulation line whatever the volume of haemorrhagic fluid to treat.

during the treatment of a determined volume of haemorrhagic fluid, the outlet of the treatment pouch is obstructed, then a dilution fluid intended to pass through the filtration device is injected into the circulation line so as to eliminate haemorrhagic fluid present in the circulation line, then treated haemorrhagic fluid present in the treatment pouch is isolated when the fluid present in the circulation line has a haematocrit level below a threshold value.

According to another preferred but non-limiting aspect of this method for using the treatment system, taken alone or in combination with the preceding aspects, cleaning is carried out—before and/or after counterflow cleaning—of the filtration membrane by rinsing, the rinsing being carried out by obstructing the outlet of the treatment pouch, by obstructing the discharge line at the level of the outlet of the discharge chamber of the filtration device, and by injecting into the intake chamber a dilution fluid intended to pass through the filtration device.

A system is furthermore proposed for treating haemorrhagic fluid previously taken from a patient for the purpose of autotransfusion, comprising a unit for treating haemorrhagic fluid, said treatment unit comprising:

a filtration device comprising a filtration membrane for tangential filtration arranged in a housing so as to separate an intake chamber from a discharge chamber, the intake chamber and the discharge chamber each having an inlet and an outlet for fluids;

a treatment pouch having an inlet and an outlet fluidically connected by a recirculation line to the outlet and to the inlet of the intake chamber of the filtration device, respectively, allowing haemorrhagic fluid to circulate in the recirculation line in a direction going from the outlet of the treatment pouch to the inlet of the treatment pouch through the intake chamber of the filtration device;

an intake line fluidically connected to the recirculation line between the outlet of the treatment pouch and the inlet of the intake chamber of the filtration device making it possible to supply the treatment unit with haemorrhagic fluid taken for the purpose of filtration through the filtration membrane of the filtration device in order to remove from the haemorrhagic fluid a filtrate comprising compounds undesired for autotransfusion;

a transfusion line fluidically connected to the recirculation line between the outlet of the treatment pouch and the inlet of the intake chamber of the filtration device making it possible to recover treated haemorrhagic fluid contained in said treatment pouch;

a discharge line fluidically connected to the outlet of the discharge chamber of the filtration device so as to discharge filtrate having traversed the filtration membrane from the intake chamber;

characterised in that the treatment unit further comprises a first flow regulation member arranged to regulate the flow in the recirculation line at the outlet of the treatment pouch, and a dilution line intended to convey a dilution fluid into the treatment unit, the dilution line being fluidically connected to the recirculation line at a position between the outlet of the treatment pouch and the inlet of the intake chamber of the filtration device.

Preferred but non-limiting aspects of this treatment system, taken alone or in combination, are the following:

an optical sensor is arranged at the level of the inlet of the treatment pouch to detect the nature of the fluid arriving at the level of the inlet.

the treatment pouch comprises a separating device being able to be actuated to separate the treatment pouch into a first treatment chamber on the side of the inlet of the treatment pouch and a second treatment chamber on the side of the outlet of the treatment pouch.

the treatment unit comprises a second flow regulation member arranged to regulate the flow in the dilution line, and a third flow regulation member arranged to regulate the flow in the recirculation line at the inlet of the intake chamber of the filtration device.

the treatment pouch has a substantially parallelepiped shape with the inlet and the outlet on either side of the treatment pouch along a diagonal, the treatment pouch further having an inner cavity having a tapering shape on the output side.

the filtration membrane of the filtration device is a filtration membrane with hollow fibres, said hollow fibres forming the filtration membrane extending longitudinally in the housing.

the filtration membrane with hollow fibres of the filtration device comprises hollow fibres formed from a mixture of polyester sulfone and polyvinyl pyrrolidone.

the filtration membrane of the filtration device has an overall porosity comprised between 0.1 μm and 1 μm, preferably of the order of 0.6 μm.

the filtration membrane of the filtration device has an overall filtration surface area comprised between 0.1 $m^2$ and 1 $m^2$, and preferably comprised between 0.2 $m^2$ and 0.6 $m^2$.

the treatment system comprises at least one peristaltic pump arranged so as to make haemorrhagic fluid circulate in the recirculation line in a direction going from the outlet of the treatment pouch to the inlet of the treatment pouch through the intake chamber of the filtration device.

the treatment system comprises a plurality of regulation valves, each regulation valve being respectively intended to cooperate with one of the regulation members in order to regulate the corresponding flow.

the treatment unit comprises a template enabling fixation of the intake line, the discharge line, the recirculation line, the dilution line, and the transfusion line.

the treatment system comprises a support unit, the template of the treatment unit having a mistake-proofing shape making it possible to couple the treatment unit to the support unit according to a unique positioning.

the support unit forms a horizontal support plane, the filtration device of the treatment unit being intended to be coupled to the support unit such that hollow fibres of the filtration membrane extend along a direction not comprised in the horizontal support plane.

the treatment system comprises a transfusion unit, said transfusion unit comprising a transfusion pouch having an inlet intended to be connected to the transfusion line in order to collect treated haemorrhagic fluid coming from the treatment pouch before transfusion to the patient.

the treatment system comprises a filtrate recovery unit, said recovery unit comprising a recovery pouch having an inlet intended to be fluidically connected to the discharge line, said recovery pouch being further intended to be coupled to a device for depressurising the recovery pouch so as to make filtrate circulate from the discharge chamber of the filtration device to the recovery pouch through the discharge line.

the treatment system comprises a filtrate recovery unit, said recovery unit comprising a recovery pouch having an inlet intended to be fluidically connected to the discharge line, said recovery pouch being further arranged with respect to the filtration device of the treatment unit to create a vacuum pressure in the recovery pouch with respect to the filtration device so as to make filtrate circulate from the discharge chamber of the filtration device to the recovery pouch through the discharge line.

the treatment system comprises a unit for collecting haemorrhagic fluid comprising a receptacle for collecting haemorrhagic fluid previously taken from the patient, said collection receptacle having an outlet fluidically connected to the intake line, said collection receptacle preferably integrating a prefiltration device making it possible to carry out prefiltration of haemorrhagic fluid before being transmitted into the treatment unit.

the treatment system further comprises an additional prefiltration device placed in the intake line.

A method is also proposed for using this system for treating haemorrhagic fluid previously taken from a patient for the purpose of later autotransfusion wherein, after partial or total treatment of haemorrhagic fluid with the filtration device, a dilution fluid is injected from the dilution line into the circulation line in order to pass through the filtration device.

According to a preferred aspect of this method for using the treatment system, cleaning of the filtration membrane is carried out by rinsing, the rinsing being carried out by obstructing the outlet of the treatment pouch at the level of the first flow regulation member, by obstructing the discharge line at the level of the second flow regulation member and by injecting cleaning fluid into the intake chamber from the dilution line.

In this case, rinsing may be stopped as soon as the optical sensor detects the presence of dilution fluid.

In a preferred manner, before rinsing, it is possible to control the separating device in order to isolate treated haemorrhagic fluid in the second treatment chamber.

According to another preferred aspect of this method for using the treatment system, in a complementary or alternative manner, a dilution of the haemorrhagic fluid contained in the treatment system is carried out, the dilution being carried out by obstructing the outlet of the treatment pouch at the level of the first flow regulation member, then by injecting cleaning fluid into the intake chamber from the dilution line, then by isolating the treated haemorrhagic fluid present in the treatment pouch when the fluid present in the circulation line has a haematocrit level below the threshold value.

DESCRIPTION OF THE DRAWINGS

Other characteristics and advantages of the invention will become clear from the description that follows, which is purely illustrative and non-limiting and which should be read with regard to the appended drawings, in which.

DETAILED DESCRIPTION OF THE INVENTION

Figure 1:
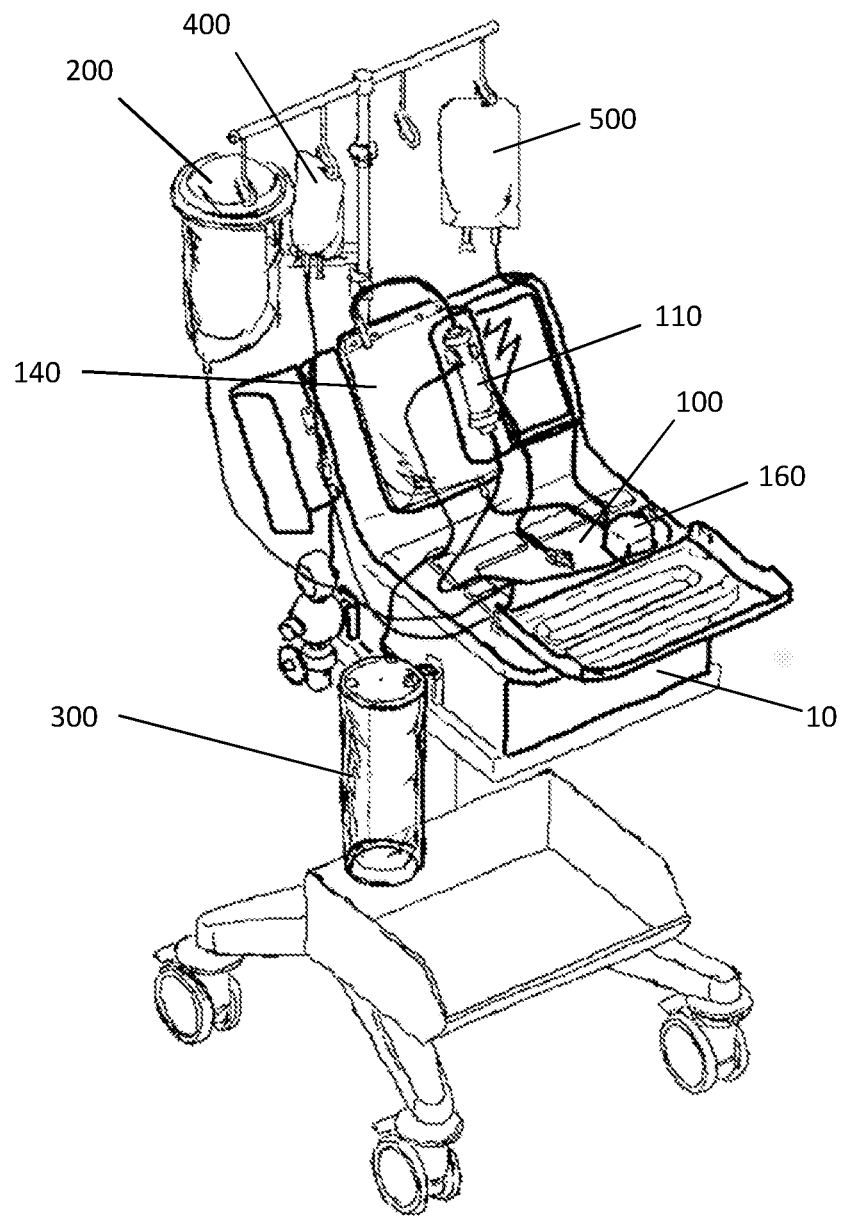
FIG. 1 is a schematic perspective view of a treatment system according to the invention.

Description of the System for Treating Haemorrhagic Fluid for the Purpose of Autotransfusion FIG. 1 illustrates a non-limiting example of a system for treating haemorrhagic fluid, notably blood, of a patient notably for the purpose of autotransfusion.

The proposed treatment system comprises a certain number of functional units, removable with respect to each other to facilitate the use thereof by practitioners, notably during a surgical intervention.

One of the particularities of the proposed treatment system resides in the unit for treating blood 100, which will be described in detail hereafter.

The proposed treatment system preferably comprises a support unit 10 which may be is various forms, with notably as represented in FIG. 1 a main support body being able to be mounted on castors. Preferably, the support unit 10 integrates the non-consumable elements of the treatment system, that is to say being able to be reused during several successive treatment cycles, in particular the elements of the system not being in direct contact with haemorrhagic fluid of the patient or any other substance which could lead to contamination.

The support unit 10 may notably integrate data processing means, in the form of one or more processors for example, but also control means making it possible to manage the treatment of haemorrhagic fluid as a function of predetermined treatment parameters and/or as a function of control information entered by the user of the system. In this respect, the support unit 10 may comprise means for inputting control information, such as a keyboard, tactile actuators, a voice recognition system or others. Preferably, information dissemination means are also provided to inform the user of the treatment cycle, these information dissemination means being able to be visual, audio and/or tactile, comprising for example a screen, lamps or light emitting diodes, a loudspeaker, a vibrator or others.

The support unit 10 also preferably integrates elements for the energy supply, notably electric, of the treatment system. The support unit 10 could integrate a battery to supply energy to the system, and it comprises whatever the case electrical connectors making it possible to connect said support unit 10 to an electrical socket, for example a wall socket of a hospital.

The circulation of fluids in the treatment system is achieved by fluid feed means which are integrated in the support unit 10 or external.

As fluid feed means, one or more peristaltic pumps 160 may for example be provided making it possible to move fluid present in a circulation circuit of the treatment system, in a specific direction of displacement of the fluid, but also possibly in the opposite direction. Preferably, the or said peristaltic pumps are integrated in the support unit 10, where they may be directly supplied electrically. The fluid feed means are preferably provided to enable circulation of haemorrhagic fluid in the treatment unit 100 with a flow rate comprised between 10 ml/min and 4000 ml/min, preferably between 100 ml/min to 2000 ml/min, and further preferably between 200 ml/min to 1400 ml/min.

Among fluid feed means, vacuum systems may also be provided, which are connected to the fluid circulation circuit to create vacuum pressures favouring the displacement of the fluid in the circulation circuit in a specific direction of displacement. In this respect, one or more vacuum pumps could be integrated in the treatment system, and more specifically in the support unit 10 in order to create the required vacuum pressures. It may also be provided that the treatment system comprises connectors enabling connection with vacuum wall sockets of the place where the treatment system is used, and also vacuum regulators so that the vacuum can be controlled specifically. Preferably, means making it possible to apply a vacuum of 0 to −100 kPa are provided.

The support unit 10 may further integrate other elements being able to be reused during several successive treatment cycles and which are functionally linked to the operations carried out by the treatment unit 100, which will be detailed hereafter.

Thus, the support unit may integrate flow regulation valves, such as solenoid valves operating for example with electromagnets or stepper motors, which are arranged to cooperate with the pipes of the treatment unit 100 to enable regulation of the flow of fluid circulating in said treatment unit 100.

Sensors may also be provided making it possible to monitor the evolution of the treatment during a specific treatment cycle. Such sensors may for example comprise pressure sensors, weighing devices, sensors notably optical sensors to calculate the haematocrit (e.g. to calculate the haematocrit level of the fluid circulating in the treatment unit).

As specified above, these reusable elements are preferably integrated in the support unit 10 but it could also be envisaged that the treatment unit 100 integrates one or more thereof.

The treatment system further comprises a unit for collecting 200 haemorrhagic fluid which is suited to being positioned on the support unit 10 as illustrated in FIG. 1.

Such a collection unit 200 comprises a receptacle for collecting 210 haemorrhagic fluid taken from the patient, for example during a surgical intervention, or beforehand.

Figure 2:
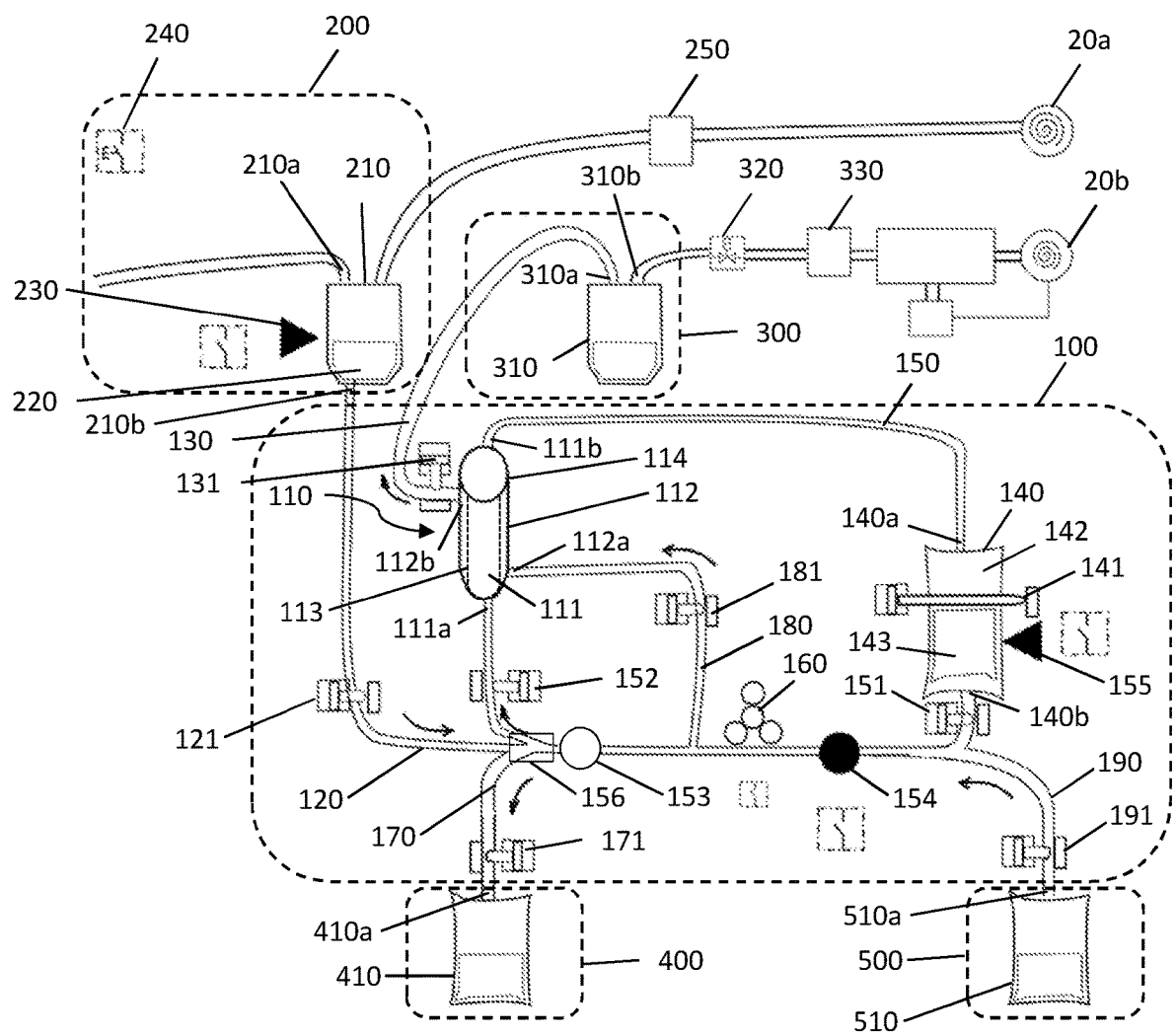
FIG. 2 is a schematic representation of a first layout of fluid connections for the treatment system according to the invention.

As may be seen illustrated in FIG. 2, this collection receptacle 210 has an outlet 210b fluidically connected to an intake line 120 provided in the treatment unit 100.

It also comprises an inlet 210a intended to be coupled to means for taking blood known per se, generally comprising a cannula for sucking up haemorrhagic fluid and notably means for dosing diluting and anticoagulant agents. A specific source of these diluting and/or anticoagulant agents, such as for example a heparinised crystalloid composition, could be connected directly to the inlet 210a of the collection receptacle 210.

Further preferably, the collection receptacle 210 integrates a prefiltration device 220 making it possible to carry out prefiltration of haemorrhagic fluid taken before being transmitted into the treatment unit 100. Such prefiltration is generally intended to filter particles of relatively large dimensions, to remove for example blood clots, pieces of bone or even pieces of tissues present in the haemorrhagic fluid taken.

Prefiltration is notably carried out to retain particles having a size greater than several tens of micrometres.

It is possible for example to use a prefiltration device 220 of frontal filtration type having a porosity gradient to retain particles of decreasing sizes, the porosity gradient ranging for example progressively from 150 μm to 40 μm.

This prefiltration device 220 may for example be a multilayer type filter, more specifically with a woven mesh layer to retain the largest elements, a non-woven mesh layer of which the thickness will make it possible to retain by steric hindrance elements of smaller size, and a final finely woven mesh layer to retain the smallest elements.

In a preferred manner, the collection unit 200 is further connected to a vacuum source, for example to a vacuum wall socket 20a via a vacuum regulator 250, to optimise prefiltration with the prefiltration device 220.

A weighing system 230, such as a force sensor forming a weight indicator, may further be provided in the collection unit 200, provided to measure the quantity of collected haemorrhagic fluid present in the collection receptacle 210. This weighing system 230 is going to make it possible to provide information for controlling the treatment cycle, making it possible for example to start a treatment cycle when the collection receptacle 210 contains sufficient haemorrhagic fluid to start a treatment cycle. The weighing system 230 also makes it possible to control the quantity of haemorrhagic fluid injected into the treatment unit 100.

The treatment system further comprises a transfusion unit 400 which is intended to be arranged on the support unit 10 and coupled to the transfusion line 170 of the treatment unit 100.

More specifically, the transfusion unit 400 comprises a transfusion pouch 410 having an inlet 410a intended to be connected to the transfusion line 170 in order to collect treated haemorrhagic fluid coming from a treatment pouch 140 integrated in the treatment unit 100, before transfusion to the patient. More specifically, when it is wished to carry out a transfusion on the patient, it is important to disconnect the transfusion pouch 410 from the treatment system and to connect it to the patient for transfusion of treated haemorrhagic fluid.

The treatment system also comprises a recovery unit 300 also mounted on the support unit 10 and intended to recover filtrate coming from the treatment unit 100, that is to say wastes withdrawn from the haemorrhagic fluid not suitable for transfusion to the patient.

This recovery unit 300 thus comprises a recovery pouch 310 having an inlet 310a intended to be fluidically connected to the discharge line 130 of the treatment unit 100.

Preferentially, the recovery pouch 310 is further provided to be depressurised so as to drive circulating fluid from the discharge line 130 up to said recovery pouch 310.

For this purpose, the recovery pouch 310 may be coupled to a depressurisation device, such as for example a vacuum system using a vacuum wall socket 20b and a vacuum regulator 330 and/or an autonomous system comprising at least one vacuum pump and an electronic regulator. A fine control of the applied vacuum makes it possible to manage the applied vacuum pressure, to avoid it being too low and that the treatment is slowed down, or to avoid it being too high which could damage the red blood cells or the filter. A shut-off and breathing valve 320 may also be provided to disengage the vacuum system as needed.

Alternatively or in addition, the depressurisation of the recovery pouch 310 may be created by a specific layout with respect to the treatment unit 100, notably by a difference in height between the two units. As may be seen represented in FIG. 1 for example, the recovery unit 300 is preferably arranged in the lower part of the support unit 10, close to the castors for example, whereas the treatment unit 100 is arranged in the upper part, or at least at a level higher than the recovery unit 300. It is to be noted that depressurisation of the recovery pouch 310 by the simple layout of the elements with respect to each other, without use of an artificial vacuum (with a vacuum pump for example) may be advantageous notably for limiting haemolysis risks.

A vertical distance separating the treatment unit 100 from the recovery unit 300 of at least 10 cm, preferably comprised between 20 cm and 100 cm, preferably comprised between 30 cm and 70 cm, and further preferably comprised between 30 cm and 60 cm may for example be provided.

Specifically, when the depressurisation of the recovery pouch 310 is uniquely created by the specific layout with respect to the treatment unit 100, the vertical distance separating the treatment unit 100 from the recovery unit 300 is preferably chosen greater than 30 cm, for example comprised between 50 cm and 70 cm, preferably comprised between 60 cm and 65 cm, and further preferably of the order of 65 cm. One of the particularities of the proposed treatment system resides in the treatment unit 100, removable with respect to the support unit 10, so as to be able to be replaced easily and rapidly, for each new patient, and having a configuration making it possible to perform a rapid treatment of haemorrhagic fluid taken without having the drawbacks of systems existing in the prior art, notably those based on centrifugation.

It is to be noted that all the elements of the treatment system which are intended to be in contact with haemorrhagic fluid to treat, which are qualified as consumables, are removable with respect to the support unit 10, and may thus be replaced very easily. Apart from the treatment unit 100, this concerns notably the collection unit 200, the recovery unit 300, and the transfusion unit 400.

The proposed treatment unit 100 is provided to enable efficient treatment of haemorrhagic fluid of a patient and to be used several times successively for a same patient, in order to be able to carry out several treatment cycles and thus to treat a greater quantity of haemorrhagic fluid.

As explained above, it is preferable to carry out tangential filtration, that is to say filtration where the haemorrhagic fluid to filter circulates parallel to a filtration membrane and is filtered on contact with this filtration membrane.

For this purpose, the proposed treatment unit 100 thus comprises a filtration device 110 for tangential filtration having a filtration membrane 113 arranged in a housing 114 so as to separate an intake chamber 111 from a discharge chamber 112, the intake chamber 111 and the discharge chamber 112 each having an inlet (111a; 112a) and an outlet (111b; 112b) for fluids. Haemorrhagic fluid to treat circulates in the intake chamber 111 from the inlet 111a to the outlet 111b and undergoes tangential filtration through the filtration membrane 113 in order to remove from the haemorrhagic fluid a filtrate comprising compounds undesired for autotransfusion. The filtrate passes through the filtration membrane 113 up into the discharge chamber 112.

Preferentially, the filtration device 110 for tangential filtration comprises a filtration membrane 113 with hollow fibres arranged in the housing 114, said hollow fibres forming the filtration membrane extending longitudinally in the housing 114. The remainder of the description is made essentially with reference to a treatment unit having a filtration device 110 with a filtration membrane 113 with hollow fibres but the corresponding teaching could apply to all types of tangential filtration device, notably with regard to problems of clogging following successive filtrations.

In a preferred manner, the filtration membrane 113 with hollow fibres of the filtration device 110 comprises fibres formed in a material having properties favouring its hydrophilicity. The fact that the filtration membrane 113 has increased hydrophilicity notably makes it possible to reduce the phenomenon of clogging of the membrane which takes place as filtration proceeds. Reducing fouling of the filtration membrane 113 makes it possible to maintain the enhanced efficiency of the filtration device 110.

Thus, preferably the hollow fibres of the filtration membrane 113 are formed from a mixture of polyester sulfone (PES) and polyvinyl pyrrolidone (PVP). For example, a membrane made of PES which has been mixed with PVP before extrusion of the fibre is provided. The basic material of the hollow fibres could also be chosen among other biocompatible materials commonly used as blood filtration membranes, such as for example, apart from PES, polymethyl methacrylate (PMMA), acrylonitrile based co- or terpolymer.

The filtration membrane 113 with hollow fibres of the filtration device 110 furthermore preferably has an overall porosity comprised between 0.1 μm and 1 μm. Such a pore size makes it possible to allow proteins and other drug molecules which are unfit to be transfused to pass through, while making it possible to conserve the compounds of interest of the haemorrhagic fluid, namely red blood cells, white blood cells and platelets.

In the proposed filtration device 110, the filtration membrane 113 has for example an overall filtration surface area greater than 0.04 $m^2$, for example comprised between 0.1 $m^2$ and 3 $m^2$, and preferably comprised between 0.2 $m^2$ and 0.6 $m^2$. More specifically, the filtration surface area is chosen sufficient so as to both enable rapid filtration of haemorrhagic fluid, typically in 5 minutes or less, but not too important in order to avoid too great protein adhesion and thus associated loss of platelets. Preferably, the filtration device enabling filtration in less than 5 min for the treatment of a volume of 500 ml of haemorrhagic fluid is chosen.

The filtration device may according to a first example comprise a filtration membrane with hollow fibres arranged longitudinally in a cylindrical housing, the filtration membrane having an average porosity of 0.6 μm, a filtration surface area of 0.2 $m^2$, said hollow fibres being formed from a mixture of polyester sulfone (PES) and polyvinyl pyrrolidone (PVP), having an inner diameter of 300 μm, an outer diameter of 470 μm, and a wall of 85 μm thickness.

According to a second example, the filtration device has the same characteristics as according to the first example but with a filtration surface area of 0.6 $m^2$.

According to a third example, the filtration device has the same characteristics as according to the first example but with a filtration surface area of 0.4 $m^2$.

The treatment unit 100 further comprises a treatment pouch 140 which is fluidically connected to the filtration device 110 by a recirculation line 150.

More specifically, the treatment pouch 140 has an inlet 140a and an outlet 140b fluidically connected by a recirculation line 150 to the outlet 111b and to the inlet 111a of the intake chamber 111 of the filtration device 110, respectively.

This layout notably enables circulation of haemorrhagic fluid in the recirculation line 150 in a direction going from the outlet 140b of the treatment pouch 140 to the inlet 140a of the treatment pouch 140 through the intake chamber 111 of the filtration device 110.

Figure 5:
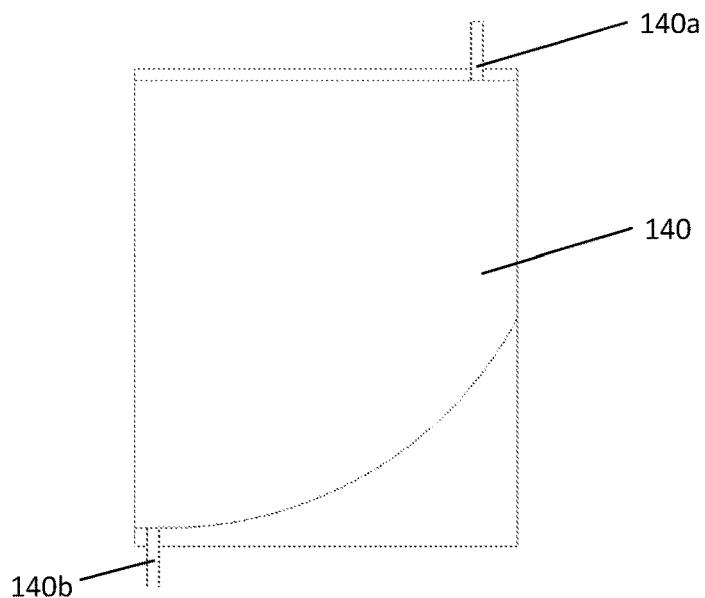
FIG. 5 is a schematic representation of a treatment pouch for the treatment unit of a treatment system according to the invention.

The treatment pouch 140 has a shape which is also provided to favour internal flow from the inlet 140a to the outlet 140b and favour mixing of the treated bloody fluid at the expense of a sedimentation effect and favoured circulation at the bottom of the pouch. For example, as illustrated in FIG. 5, The treatment pouch 140 has a substantially parallelepiped shape with the inlet 140a and the outlet 140b on either side of the treatment pouch along a diagonal. Further preferably, the treatment pouch further has an inner cavity having a tapering shape on the side of the outlet 140b, so as to make fluid contained in the treatment pouch 140 converge towards the outlet 140b.

This treatment pouch 140 has an active role in the cycle for treating haemorrhagic fluid. Firstly, as will be seen hereafter, it enables recirculation of haemorrhagic fluid during a treatment cycle, that is to say several successive circulations in the filtration device 110, without variation of the circulation flow rate of haemorrhagic fluid during said treatment cycle. It in fact plays the role of buffer zone which makes it possible to absorb potential flow variations. The treatment pouch 140 could also be used as zone for mixing haemorrhagic fluid to treat with a dilution fluid in order to favour filtration and the elimination of soluble elements such as proteins and drug substances through the filtration device 110.

The treatment pouch 140 may be equipped, without this being obligatory, with a separating device 141 being able to be actuated to separate the treatment pouch 140 into a first treatment chamber 142 on the side of the inlet 140*a* of the treatment pouch 140 and a second treatment chamber 143 on the side of the outlet 140*b* of the treatment pouch 140. Such a separating device 141 may for example take the form of an electromechanical clamp being able to be actuated to form said first and second treatment chambers as a function of the unwinding of the treatment cycle.

The fluid feed means of the support unit 10 are provided mainly to ensure circulation of haemorrhagic fluid in the direction cited previously—called direction of treatment—going from the outlet 140*b* of the treatment pouch 140 to the inlet 140*a* of the treatment pouch 140 through the intake chamber 111 of the filtration device 110. They may optionally also enable circulation in the opposite direction for certain specific phases of the treatment cycle as will be seen hereafter.

According to the exemplary embodiment of FIG. 2, a peristaltic pump 160 is provided in the recirculation line positioned in the recirculation line 150 between the outlet 140*b* of the treatment pouch 140 and the inlet 111*a* of the intake chamber 111 of the filtration device 110. This makes it possible to make haemorrhagic fluid circulate in both the directions of circulation specified above.

The treatment unit 100 furthermore comprises various conduits allowing fluid to circulate within the actual treatment unit 100 with the circulation line 150 mentioned previously, but also to/from the other units of the treatment system.

Thus, the treatment unit 100 comprises an intake line 120 fluidically connected to the recirculation line 150 between the outlet 140*b* of the treatment pouch 140 and the inlet 111*a* of the intake chamber 111 of the filtration device 110 making it possible to supply the treatment unit 110 with haemorrhagic fluid taken for the purpose of filtration through the filtration membrane 113 with hollow fibres of the filtration device 110 in order to remove from the haemorrhagic fluid a retentate comprising compounds undesired for autotransfusion. This intake line 120 is furthermore intended to be connected, removably, to the collection unit 200 described above.

Figure 7:
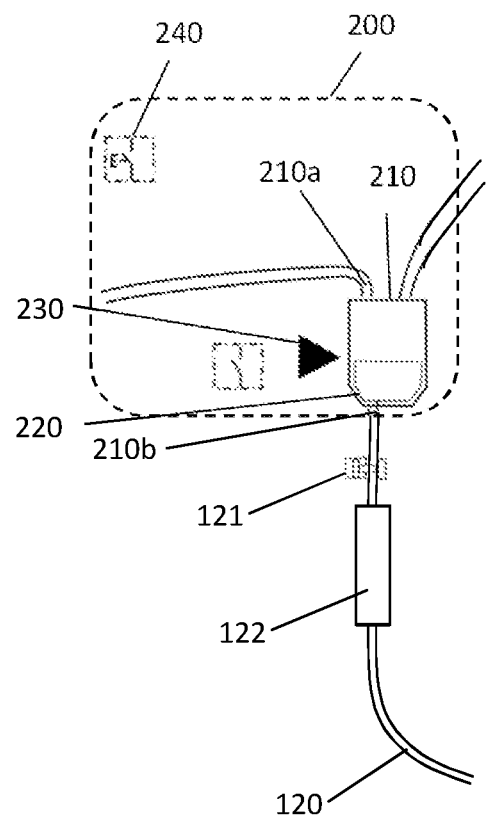
FIG. 7 is a schematic representation illustrating an example of positioning of an additional prefiltration device for the treatment system described.

As illustrated in FIG. 7, it may be provided to interpose in this intake line 120, on the side intended to be connected to the collection unit 200, an additional prefiltration device 122 making it possible to carry out additional filtration before the actual filtration by the filtration device 110 of the treatment unit 100. The purpose of such an additional prefiltration device 122 is to retain the mass of coagulated substance, called coagulum, which is liable to form at the outlet of the collection receptacle 210 despite the optional prefiltration device 220.

The additional prefiltration device 122 operates as a dynamic filter, that is to say that it must be able to operate with the flow rates imposed by the treatment unit, without adversely affecting the treatment time performances. The additional prefiltration device 122 preferably has a level of filtration higher than the level of filtration of the optional prefiltration device 220 of the collection receptacle 210.

The additional prefiltration device 122 may for example have a level of filtration comprised between 40 μm and 200 μm, preferably comprised between 100 μm and 170 μm, further preferably of the order of 150 μm. The coagulum retention volume may be comprised between 5 ml and 100 ml, and preferably comprised between 20 ml and 50 ml.

Preferably, this additional prefiltration device 122 forms an integral part of the treatment unit 100. It may however also be envisaged that this additional prefiltration device is integrated in the collection unit 200, at the level of the outlet of the collection receptacle 210.

Preferably, this additional prefiltration device 122 is mounted removably in the treatment system, which makes it possible for example to be able to remove it and to clean it in the event of clogging.

The treatment unit 100 further comprises a transfusion line 170 also fluidically connected to the recirculation line 150 between the outlet 140*b* of the treatment pouch 140 and the inlet 111*a* of the intake chamber 111 of the filtration device 110, and making it possible to recover treated haemorrhagic fluid contained in said treatment pouch 140. This transfusion line 170 is furthermore intended to be connected, removably, to the transfusion unit 400 described above.

Figure 3:
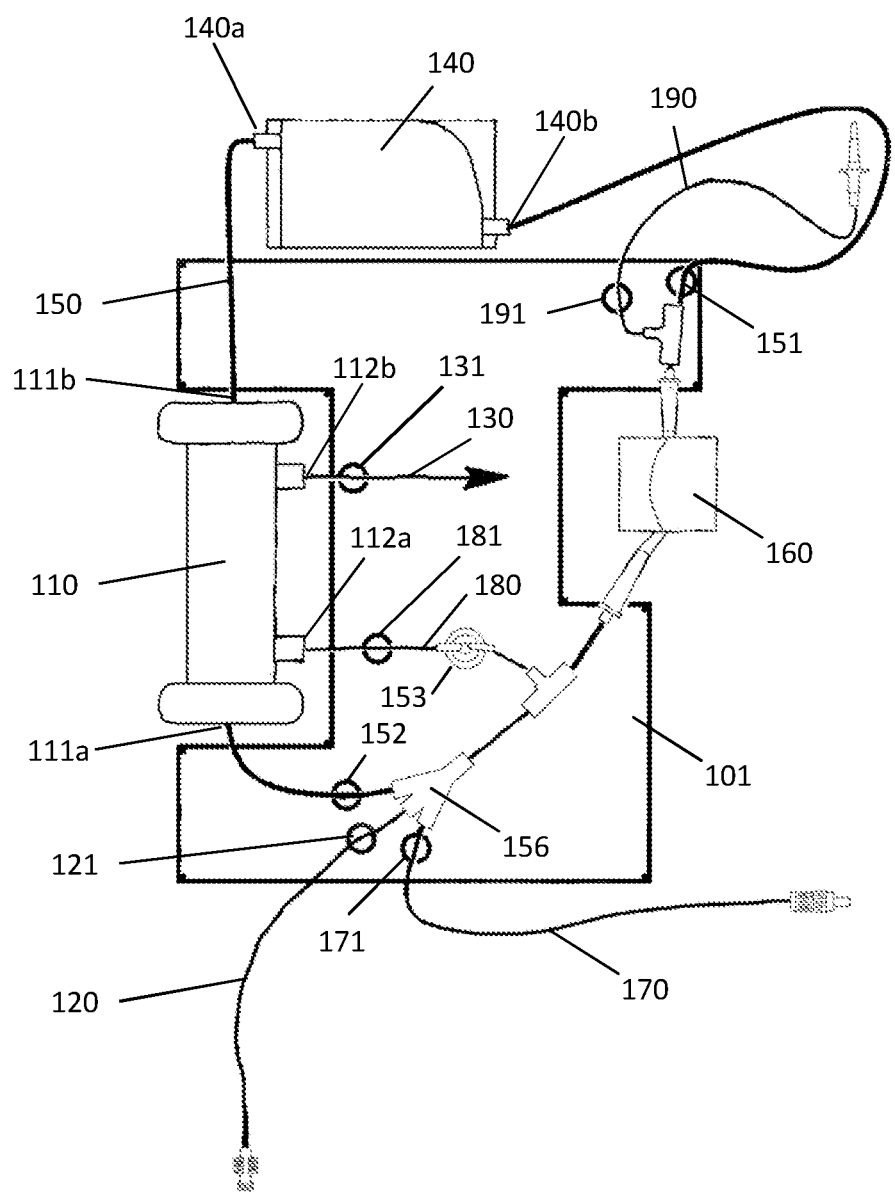
FIG. 3 is a representation of a treatment unit of a treatment system, according to a first embodiment of the first layout.
Figure 4:
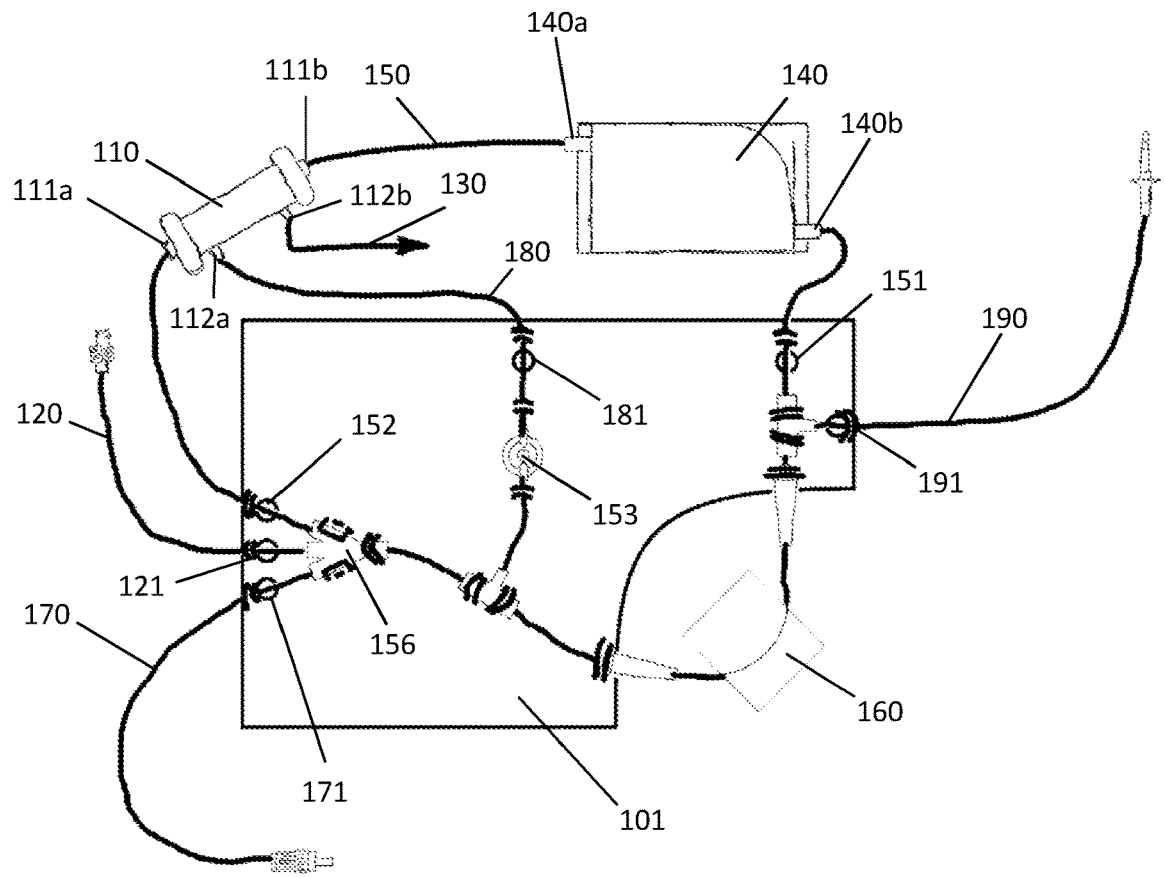
FIG. 4 is a representation of a treatment unit of a treatment system, according to a second embodiment of the first layout.

In a preferred manner, the intake line 120 and the transfusion line 170 are tapped at the same position on the recirculation line 150 as illustrated in FIG. 2, with for example a multipath fluidic connector 156. A 3-way connector 156 may thus be used as illustrated in FIGS. 2, 3, and 4, with an inlet path fluidically connected to the recirculation line 150 in the direction of the outlet 140*b* of the treatment pouch 140, a first outlet path fluidically connected to the recirculation line 150 in the direction of the inlet 111*a* of the intake chamber 111 of the filtration device 110, a second outlet fluidically connected to the intake line 120, and a third outlet fluidically connected to the transfusion line 170.

Figure 6:
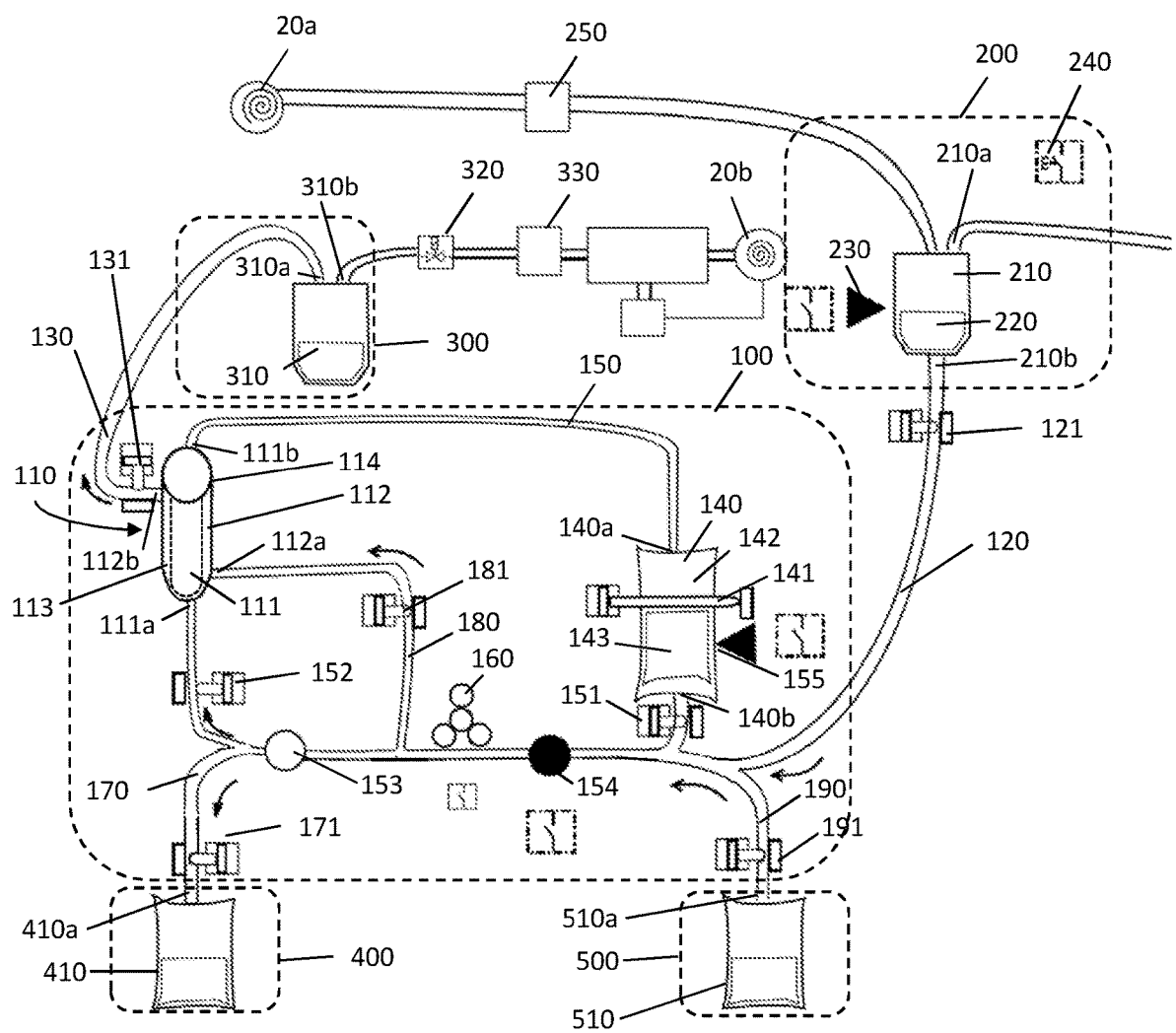
FIG. 6 is a schematic representation of a second layout of the fluid connections for the treatment system according to the invention.

As will be seen hereafter, and as illustrated in FIG. 6, it could however be provided that the intake line is tapped upstream of the peristaltic pump 160, at the level of the outlet 140*b* of the treatment pouch 140. In this case, the transfusion line is connected to the recirculation line by a standard 2-way fluidic connector. In this case, it is not necessary that the peristaltic pump 160 is suited to make haemorrhagic fluid circulate in both directions of circulation and it is sufficient to have a pump allowing haemorrhagic fluid to circulate along a single direction, namely the direction of treatment.

The treatment unit 100 furthermore comprises a discharge line 130 fluidically connected to the outlet 112*b* of the discharge chamber 112 of the filtration device 110 so as to discharge filtrate having traversed the filtration membrane 113 with hollow fibres from the intake chamber 111. This discharge line 130 is furthermore intended to be connected, removably, to the discharge unit 130 described above.

When the recovery pouch 310 is provided to be depressurised, by a vacuum system for example, this makes it possible to accelerate filtration through the filtration membrane 113 of the filtration device 100 since said vacuum pressure is felt through the discharge line 130 up into the discharge chamber 112.

The treatment unit 100 may furthermore comprise a cleaning line 180 fluidically connected to the inlet 112*a* of the discharge chamber 112 of the filtration device 110 to convey cleaning fluid into said discharge chamber 112. It is to be noted that this cleaning line 180 is not obligatory in all the exemplary embodiments described.

The objective of this cleaning line 180 is to make it possible to convey a fluid into the discharge chamber 112 and to create transmembrane counterflow, that is to say a flow going in a direction opposite to the normal direction of flow through the filtration membrane 113 with hollow fibres of the filtration device 110 during filtration. This counterflow through the filtration membrane 113 is very useful for removing all or part of the elements retained on the hollow fibres of the filtration membrane 113, and thus regenerating the filtration capacities of the filtration membrane 113 notably in terms of efficiency and rapidity of filtration. The proposed counterflow is also advantageous in that it enables cleaning of the filtration membrane in a simple and rapid manner, during a treatment cycle or between two treatment cycles.

A flow regulation member 181 may be provided arranged to regulate the flow in the cleaning line 180 and another flow regulation member 131 arranged to regulate the flow in the discharge line 130 so as to be able to control the pressure of cleaning fluid in the discharge chamber 112.

Counterflow may thus be created by obstructing the discharge line 130 at the level of the flow regulation member 131 and by injecting cleaning fluid into the discharge chamber 112 from the cleaning line 180, the pressure created in the discharge chamber 112 by the injection of cleaning fluid creating the required transmembrane counterflow.

Cleaning fluid may be injected directly into the cleaning line 180 when this is required to create counterflow, an external source containing cleaning fluid then being provided.

Whether the treatment unit 100 comprises a cleaning line 180 or not, a dilution line 190 may further be provided making it possible to convey a dilution fluid into the treatment unit 100. The dilution line 190 is then preferably fluidically connected to the recirculation line 150 at a position between the outlet 140b of the treatment pouch 140 and the inlet 111a of the intake chamber 111 of the filtration device 110. Preferably, the dilution line 190 is tapped upstream of the peristaltic pump 160.

This dilution line 190 is furthermore intended to be connected, removably, to a dilution unit 500 comprising a dilution receptacle 510 having an inlet/outlet orifice 510a intended to be coupled to the dilution line. The dilution receptacle 510 contains the dilution fluid which is intended to be injected into the treatment unit 100. This dilution fluid may be a crystalloid composition, preferably an isotonic solution compatible with erythrocytes, without carbohydrates or proteins, comprising for example sodium chloride, sodium lactate, and/or potassium chloride diluted in water to produce an injectable preparation.

A flow regulation member 191 is preferably provided to enable flow regulation in the dilution line 190.

In a preferred manner, the cleaning line 180 is fluidically connected to the recirculation line 150 at a position between the outlet 140b of the treatment pouch 140 and the inlet 111a of the intake chamber 111 of the filtration device 110. When the treatment unit 100 comprises a dilution line 190 then the dilution fluid may be used to supply the cleaning line 180 and thus be used as cleaning fluid.

Preferably, another flow regulation member 151 is provided in the treatment unit 100 and arranged to regulate the flow in the recirculation line 150 at the level of the outlet 140b of the treatment pouch 140.

Yet another flow regulation member 152 is preferably provided so as to be able to regulate the flow in the recirculation line 150 at the level of the inlet 111a of the intake chamber 111 of the filtration device 110.

A flow regulation member 171 arranged to regulate the flow in the transfusion line 170 may also be provided, thus making it possible to control the flow to transmit to the transfusion unit 400.

The exemplary embodiment presented in FIGS. 2 to 4 and 6 is a treatment system of which the treatment unit 100 necessitates a single peristaltic pump 160 for the circulation of fluids in the circuit, this peristaltic pump 160 being arranged so as to make haemorrhagic fluid circulate in the recirculation line 150 in a direction—designated direction of treatment—going from the outlet 140b of the treatment pouch 140 to the inlet 140a of the treatment pouch 140 through the intake chamber 111 of the filtration device 110.

Preferentially, this peristaltic pump 160 makes it possible to make the flow also circulate in a direction opposite to the direction of treatment, that is to say going from the inlet 111a of the intake chamber 111 of the filtration device 110 to the outlet 140b of the treatment pouch 140. This is particularly advantageous in the exemplary embodiment of FIG. 2 where the intake line 120 is tapped downstream of the peristaltic pump 160, that is to say at the level of the inlet 111a of the intake chamber 111 of the filtration device 110. Preferably, the peristaltic pump 160 is positioned in the recirculation line 150 between the outlet 140b of the treatment pouch 140 and the inlet 111a of the intake chamber 111 of the filtration device 110 between the position where the dilution line 190 is fluidically connected to the recirculation line 150 and the position where the cleaning line 180 is fluidically connected to the recirculation line 150.

As a function of the operation envisaged for the treatment unit 100, the intake line 120 is tapped on the recirculation line 150 downstream of the peristaltic pump 160 as illustrated in FIG. 2, that is to say on the side of the inlet 112a of the intake chamber 112 of the filtration device, or is tapped on the recirculation line 150 upstream of the peristaltic pump 160, that is to say on the side of the outlet 140b of the treatment pouch 140, as illustrated in FIG. 6.

In the case where the intake line 120 is tapped on the recirculation line 150 downstream of the peristaltic pump 160 as illustrated in FIG. 2, the haemorrhagic fluid will, during the launch of a treatment cycle, be preferably transmitted from the collection receptacle 210 to the treatment pouch 140.

In the case where the intake line 120 is tapped on the recirculation line 150 upstream of the peristaltic pump 160, the haemorrhagic fluid will be, during the launch of a treatment cycle, preferably transmitted from the collection receptacle 210 directly through the filtration device 110. This has the advantage of not requiring a peristaltic pump 160 having to operate in both directions of circulation of the fluid.

As has been specified above, the treatment system preferably comprises sensors making it possible to monitor the evolution of treatment during a specific treatment cycle.

In this respect, a pressure sensor 153 may be provided within the circulation line 150, notably arranged to detect overpressures downstream of the peristaltic pump 160 in the direction of treatment.

A haematocrit sensor 154 may further be provided to measure the haematocrit level of the fluid circulating in the treatment unit 100. Such a haematocrit sensor 154 may for example be an optical sensor formed of an assembly of diodes emitting in the infra-rouge and receptors.

A weighing system 155 may also be provided, such as a force sensor forming a weight indicator, arranged to measure the quantity of fluid present in the treatment pouch 140. This weighing system 155 is going to make it possible to provide information to control the treatment cycle, making it possible for example to trigger a transfer of treated haemorrhagic fluid to the transfusion unit 400 when the target parameters, notably in terms of haematocrit level, are reached.

The treatment unit 100 being a consumable, notably intended to be replaced for each new patient, it is preferable that its handling is simple and easy. Since this treatment unit 100 comprises a certain number of different components and tubing forming the fluid circulation lines, a template 101 may be provided which notably enables fixation of the intake line 120, the discharge line 130, the recirculation line 150, the transfusion line 170, as well as the cleaning line 180 and/or the dilution line 190 if need be. The filtration device 110 as well as the treatment pouch 140 are integral parts of the treatment unit 100 and are thus connected beforehand to the corresponding tubing and to the template 101. The treatment unit 100 thus proposed may thus be proposed as a consumable in kit form, to replace according to needs.

The template 101 is also provided to enable easy putting in place on the support unit 10 and has in this respect a mistake-proofing shape making it possible to couple the treatment unit 100 to the support unit 10 according to a unique positioning.

Furthermore, the filtration device 110 of the treatment unit 100 is intended to be coupled to the support unit 10 such that the hollow fibres of the filtration membrane 113 extend along a direction not comprised in the horizontal support plane defined by the support unit 10, that is to say that the filtration device 110 is inclined with respect to the horizontal support plane. It is to be noted that this horizontal support plane corresponds to the transverse plane of the support unit 10, which is parallel to the horizontal plane when the support unit 10 is laid on the ground.

The example of FIG. 3 illustrates a treatment unit 100 having a template 101 provided for vertical emplacement of the template 101, that is to say that the template 101 is fixed in a plane different from the horizontal support plane of the support unit 10, for example an inclined plane, and preferably a vertical plane (that is to say perpendicular to the horizontal support plane). According to this embodiment, the filtration device 110 may also be fixed to the template 101 since putting in place the template 101 will necessarily lead to an inclined layout of the filtration device 110.

The example of FIG. 4 illustrates a treatment unit 100 having a template 101 provided for horizontal emplacement of the template 101, that is to say that the template 101 is fixed in a plane parallel to the horizontal support plane of the support unit 10. According to this embodiment, the filtration device 110 is not fixed to the template 101 and will have to be fixed to the support unit 10 in an independent manner to be arranged inclined with respect to the horizontal support plane.

As illustrated in FIGS. 3 and 4, the flow regulation members which have been described previously may take the form of orifices arranged facing the tubing forming the fluid circulation lines where the flow must be controlled. Regulation valves are then provided, for example solenoid valves operating with electromagnets, arranged to come against the tubing through the orifices in order to control the section of the tubing and thus the flow of fluid being able to pass therethrough. In a preferred manner, these regulation valves are directly mounted on the support unit 10 and may thus be used for different successive treatment units 100.

The putting in place of the treatment unit 100 comprising a template 101 is very simple. Indeed, it suffices to position the template 101 in the housing provided for this purpose on the support. When the flow regulation members are orifices intended to cooperate with solenoid valves of the support unit 101, opposite placing is automatic thanks to the indexing pin shape of the template 101. Once the template 101 is in place on the support unit 10, it is important to connect the intake line 120 to the intake unit 200, the discharge line 130 to the discharge unit 300, the transfusion line 170 to the transfusion unit 400, and optionally the dilution line 190 to the dilution unit 500. It is to be noted that some of the units could be preconnected to their respective lines, that is to say to be already connected to the treatment unit 100 before being put in place on the support unit 10. For example, the transfusion unit 400 is preferably preconnected to the transfusion line 170, and the discharge unit 300 may also be preconnected to the discharge line 130. When the filtration device 110 and/or the treatment pouch 140 are not fixed to the template 101, it is important to fix it on the support unit 10.

The treatment flow rate is chosen sufficiently high to apply an important shear force which limits protein and platelet adhesion at the level of the filtration device, without however being too high which would create undesired haemolysis. The flow rates chosen are much greater than, generally 5 to 10 times greater than, the flow rates generally recommended for a filtration device using a filtration membrane with hollow fibres. Indeed, it has been observed that the filtration results were positive in terms of cellular concentration, and the high circulation flow rates are not bothersome since the treatment system is not connected directly to the patient, but uniquely indirectly via the collection unit 200 on the one hand and the transfusion unit 400 on the other hand when the latter are connected to the patient. In practice, as indicated above, the treatment unit 100 preferably operates with a flow rate comprised between 10 ml/min and 4000 ml/min, and preferably between 100 ml/min to 2100 ml/min, for example 1400 ml/min or 700 ml/min.

The application of a vacuum controlled to between 0 to −100 kPa at the level of the recovery unit 300 through the discharge line 130 makes it possible to improve the speed of filtration and to maintain it constant. In addition, during reversal of the transmembrane flow (notably during counterflow cleaning) de-priming of the filtration may be observed if vacuum pressure is not applied continuously, thus making the continuation of the treatment of the blood impossible.

Apart from the aforementioned advantages in terms of cleaning to extend the lifetime and the filtering efficiency of the filtration device 110, the passage of the dilution fluid to rinse the filtration membrane 113 with hollow fibres between two treatment cycles also contributes to platelet recovery.

The treatment system proposed for the treatment of haemorrhagic fluid for the purpose of autotransfusion is simple to use and enables rapid treatment of haemorrhagic fluid taken from the patient with qualitative performances greater than existing devices. All or part of the performances indicated below may indeed be reached with the proposed treatment device:

Average yield of platelets greater than or equal to 40%, or even greater than or equal to 50%, or even greater than or equal to 60%, and even greater than or equal to 70%;

Average yield of red blood cells (RBC) greater than or equal to 80%, or even greater than or equal to 90%, and even greater than or equal to 95%, or even of the order of 99%;

Average yield of white blood cells (WBC) greater than or equal to 80%, or even greater than or equal to 90%, and even greater than or equal to 95%, or even of the order of 97%;

Reduced haemolysis, or even zero or close to zero haemolysis. The target haemolysis could for example be less than 1%, preferably less than 0.8%;

Elimination of free haemoglobin greater than or equal to 95%, or even greater than or equal to 98%;

Residual concentration of heparin in the transfusion pouch after treatment less than or equal to 0.5 IU/ml.

Treatment time of a volume of 500 ml of haemorrhagic fluid to make it suitable for a transfusion which is less than or equal to 10 min, preferably less than or equal to 8 min, preferably less than or equal to 6 min, and in an optimum manner of the order of or less than or equal to 5 min.

It is to be noted that the level of qualitative performances indicated above is to be modulated as a function of the operating conditions.

For example, if the treatment has to be done very rapidly, it is possible that the performances are slightly diminished.

In the same way, if it is decided to concentrate the treated haemorrhagic fluid several times, for example during a triple concentration, in order to be certain of removing compounds undesired for autotransfusion, such as products undesirable for transfusion of heparin type, it is possible that some of the performances are diminished, without this however reducing the overall performance of the proposed treatment system compared to existing systems.

Operation of the System for Treating a Haemorrhagic Fluid for the Purpose of Autotransfusion An example of operation of the proposed treatment system is described below, according to a standard mode, and is not in any way limiting. The proposed treatment system could indeed be used in standard mode according to different specific phases, adapted as a function of the surgical intervention need or the transfusion need. The operation of the proposed treatment system may also be adapted to particular operational situations, for example in an emergency when a transfusion is necessary even if the treatment has not totally ended, or when the volume of haemorrhagic fluid to treat is not optimal for the standard treatment cycle.

The example of operation below is described with reference to the first layout of the treatment unit 100 such as illustrated in FIGS. 2 to 4. According to this layout, it is possible to dilute the haemorrhagic fluid before launching the concentration by passage through the filtration device. The volume of rinsing fluid used for the dilution may be 200 ml for a haemorrhagic fluid bolus of 500 ml, but this volume of rinsing fluid could be much higher, for example of the order of 18 litres (depending on the initial concentration of anticoagulant in the haemorrhagic fluid). This dilution volume may be added at the start of treatment or per bolus of several ml to several hundreds of ml during treatment, after a first concentration or not of the volume of haemorrhagic fluid.

In an example of operation according to the second layout of the treatment unit 100 such as illustrated in FIG. 6, the haemorrhagic fluid entering into the treatment unit is concentrated, while passing through the filtration device, before addition of rinsing fluid. Indeed, haemorrhagic fluid directly passes through the filtration device 113 during its transfer from the collection unit 200 to the treatment pouch 140. The advantage of filtration before addition of dilution fluid is direct elimination of soluble elements during transfer to the treatment pouch. In this case, the fact of being able to unclog the filtration device is particularly advantageous since it will have a tendency to foul more rapidly.

A. Phase of Preparing the Treatment System

The phase of preparing the proposed treatment system will firstly be described, comprising a phase of installing the components of the treatment system then a phase of initialising and testing this treatment system.

All the clamps formed by the solenoid valves for the regulation of fluid flows are in open position.

The collection unit 200, the recovery unit 300, the transfusion unit 400 and the dilution unit 500 are installed on the support unit 10.

The treatment unit 100 is next installed on the support unit 10. The clamp of the regulation valve 121 of the intake line 120 and that of the regulation valve 191 of the dilution line 190 are closed.

The different units are finally connected using the tubing of the corresponding fluid circulation lines, and associated connectors, these connectors being for example of "Luer Lock" type.

The collection unit 200 as well as the recovery unit 300 are connected to vacuum wall sockets (20a; 20b). A source of heparinised crystalloid solution may furthermore be connected to the inlet 210a of the collection receptacle 210.

Once all the elements have been connected to the support unit 10, the treatment system may be started up (electrical supply) and a phase of initialising and testing the treatment system is launched, managed by the central unit of the support unit 10.

In this test phase, it is verified that all the units are correctly connected to the support unit 10 and to each other. Optical contacts placed at the level of the support unit 10 may for example notably be used so that the central unit obtains this type of information.

In initialisation, a command from the central unit controls the clamps of the different lines so that the regulation valves are all in closed position.

The vacuum sources are now supplied and the treatment system is operational to launch a treatment cycle.

B. Phase of Preparing the Circuit of the Treatment Unit Before the First Treatment Cycle Before strictly speaking launching a treatment cycle, a phase of preparing the treatment cycle may be carried out, in a preferred but optional manner, which makes it possible to improve the efficiency of the actual treatment cycle.

This preparatory phase may be performed upstream of the surgical intervention, but it is preferred to do it during the surgical intervention, as soon as bleeding is observed and when autotransfusion is envisaged.

A priming of the collection unit 200 is firstly carried out by filling the collection receptacle 210 by suction of the heparinised crystalloid solution until obtaining a certain volume in said collection receptacle 210. This suction may for example be achieved by application of a vacuum in the collection receptacle 210 of the order of 300 mbar. The collection receptacle 210 is filled with for example 200 ml of heparinised crystalloid solution. This priming of the collection unit with heparinised crystalloid solution makes it possible to humidify the collection unit 200 which is going to facilitate prefiltration therewithin, in terms of speed of filtration notably. Furthermore, this makes it possible to heparinise the materials and thus limit the phenomenon of coagulation.

A priming of the recirculation line of the treatment unit 100 is then carried out in which the treatment strictly speaking is carried out. This priming may start notably when bleeding is active. To do so, the depressurisation of the recovery unit 300 is activated, for example a vacuum is applied through the filtration device 100 by activating the valve 320, whereas the regulation valve 121 of the intake line 120 and the regulation valve 191 of the dilution line 190 are closed and all the other clamps open. The clamps of the regulation valve 181 of the cleaning line 180, the regulation valve 151 of the recirculation line 150, the regulation valve 171 of the transfusion line 170 are next closed, and the clamp of the regulation valve 191 of the dilution line 190 is opened. The peristaltic pump 160 is started up and the recirculation line 150 fills with dilution fluid from the dilution unit 500. Air present in the circuit is discharged through the discharge line 130 and the dilution fluid progressively fills the different empty chambers of the elements of the treatment unit 100, in particular the filtration device 110 and the treatment pouch 140.

After a time delay for filling the recirculation line, if need be a priming of the cleaning line 180 is carried out. In this respect, while the vacuum pressure of the recovery unit 300 is still active, with for example the vacuum applied through the recovery unit 300, the clamp of the regulation valve 181 of the cleaning line 180 is opened then the clamps of the regulation valve 152 of the recirculation line 150 and the regulation valve 151 of the recirculation line 150 are closed. The dilution fluid then circulates through the cleaning line 180 up into the discharge chamber 112 of the filtration device 110 then through the hollow fibres of the filtration membrane 113 in counterflow.

This priming of the recirculation line and the cleaning line 180 of the treatment unit 100 progressively fills the treatment pouch 140 with dilution fluid.

Preferentially, these priming phases are continued until a certain volume of dilution fluid is present in the treatment pouch 140, this fluid will serve to dilute/wash the haemorrhagic fluid to treat. Preferably, the clamp of the regulation valve 131 of the discharge line 130 is closed, and the valve 320 for the vacuum is also closed, to fill more rapidly the treatment pouch 140 with dilution fluid. In the treatment pouch, filling with dilution fluid continues to reach a volume—designated washing volume—useful for the first treatment cycle. A washing volume of 200 ml is for example used when it is wished to treat a haemorrhagic fluid bolus of around 500 ml. When the weight indicator 155 of the treatment pouch 144 detects that the washing weight (=volume) is reached, the pump 160 is stopped.

It could also be envisaged not to fill the treatment pouch 140 and conversely to empty it via the discharge unit 300, after the priming phase. In this case, the dilution of the haemorrhagic fluid bolus will be carried out directly during the treatment phase, when the haemorrhagic fluid is injected into the circuit of the treatment unit 100.

The treatment unit 100 is thus ready to receive a first bolus of haemorrhagic fluid to treat and to carry out the first treatment cycle. While waiting for the collection receptacle 210 to contain a sufficient quantity of haemorrhagic fluid for the first treatment cycle (for example around 500 ml), the clamps of the regulation valve 181 of the cleaning line 180 and the regulation valve 191 of the dilution line 190 are closed, such that all the clamps are closed.

It is the weight indicator 230 of the collection receptacle 210 that will trigger the launch of the treatment when the quantity of haemorrhagic fluid to treat is sufficient.

It is to be noted that the opening/closing order of the different clamps is chosen to enable the pump to operate continuously and thus to have a continuous circulation of fluids in the treatment unit 100.

C. Phase of Treating the Haemorrhagic Fluid

In the overall autotransfusion process, there are three successive steps independent of each other:

E1. Taking haemorrhagic fluid, where an intervention on the patient is necessary. Haemorrhagic fluid is in fact taken from the patient and transferred into the collection receptacle 210 of the collection unit 200.

E2. Treatment of the haemorrhagic fluid taken, which is done without any link with the patient. This treatment step is carried out on the proposed treatment system, notably in the treatment unit 100.

E3. Transfusion of the treated haemorrhagic fluid, where an intervention on the patient is necessary. The haemorrhagic fluid which has been treated by the treatment unit 100 then transferred into the transfusion pouch 410 of the transfusion unit 400 may be transfused to the patient. To do so, it is preferable to disconnect the transfusion pouch 410 from the treatment system to connect it to the patient.

The description that follows details step E2 of treatment of haemorrhagic fluid taken previously from a patient during step E1. Whether there is a preparatory phase of the circuit of the treatment unit 100 as described above or not, the first treatment cycle will start when the volume of haemorrhagic fluid in the collection receptacle 210 has reached a threshold, this threshold preferentially corresponding to the volume of the bolus that it is wished to treat in a treatment cycle, this bolus of haemorrhagic fluid being for example chosen of the order of 500 ml.

Thus, to treat volumes of haemorrhagic fluid greater than the volume fixed for a bolus to treat during a treatment cycle, it is advisable to carry out several successive treatment cycles.

It is to be noted that the treatment cycle could, in certain particular cases, be carried out with a volume of haemorrhagic fluid less than the volume fixed for the treatment bolus, such as for example at the end of treatment where there remains less haemorrhagic fluid to treat, at the end of bleeding, or at any suitable moment chosen by the practitioner. It is however to be noted that it will be necessary all the same that the volume of haemorrhagic fluid to treat is greater than, preferably at least two times greater than, the dead volume of the treatment circuit (VmTT), that is to say the volume comprised between the outlet 140$b$ of the treatment pouch 140 and the inlet 140$a$ of the treatment pouch 140, that is to say the volume of the recirculation line 150 and the inside of the filtration device 113.

As already indicated, the treatment cycle is going to be able to be launched automatically as soon as the weight indicator 230 of the collection receptacle 210 has measured the target quantity of the bolus. This bolus may for example be equal to 500 ml of haemorrhagic fluid. This bolus could be mixed with dilution fluid stored in the treatment pouch 140 (for example a volume of 200 ml) during the phase of pre-treatment and priming of the treatment unit 100. In the case where the dilution volume is not present in the treatment pouch 140, for example when no pre-treatment phase has been launched or when treatment begins by a filtration phase in the filtration device 113, it could be possible to introduce the required volume of dilution fluid directly into the recirculation line 150 from the dilution unit 500, To mix the haemorrhagic fluid of the collection receptacle 210 with the dilution fluid present in the treatment chamber 140, it is important first of all to fill the treatment pouch 140 with said haemorrhagic fluid. To do so, the clamps of the regulation valve 121 of the intake line 120 and the regulation valve 151 of the recirculation line 150 are opened and the peristaltic pump 160 is started up in inversed rotation, that is to say to drive the haemorrhagic fluid in the direction opposite to the direction of treatment, to the outlet 140$b$ of the treatment chamber 140. When the weight indicator 155 of the treatment pouch 140 detects that the target treatment volume is reached, the peristaltic pump 160 is stopped. It is to be noted that this mixing step could be carried out by firstly injecting haemorrhagic fluid into the treatment pouch 140 or by carrying out beforehand a filtration and concentration then by injecting dilution fluid into this same treatment pouch 140 if it is not already present.

The phase of treating the haemorrhagic fluid strictly speaking may next start, with a filtration and concentration until the target haematocrit level is obtained. In general, the desired haematocrit level is of the order of 45%+/−5%, but it could be of the order of 50%+/−5%, 55%+/−5%, or even at the most 60%+/−5%. For this phase, the clamp of the regulation valve 121 of the intake line 120 is thus going to be closed then the clamps of the regulation valve 152 of the recirculation line 150 and the regulation valve 131 of the discharge line 130 opened; the electrical control valve 320 is also actuated to impose a vacuum in the discharge chamber 112 through the recovery unit 300. The peristaltic pump 160 is then actuated in the direction of treatment, such that the fluid contained in the treatment pouch 140 circulates from the outlet 140b to the inlet 111a of the intake chamber 111 of the filtration device 110, then from the outlet 111b of the intake chamber 111 of the filtration device 110 up to the inlet 140a of the treatment pouch 140.

In passing through the filtration device 110, the haemorrhagic fluid to treat is filtered by the filtration membrane 113 with hollow fibres and is progressively freed of compounds undesired for autotransfusion (such as proteins and other drug molecules which are unfit to be transfused), these pass through the filtration membrane 113 up to the discharge chamber 112 before being sucked up by the vacuum pressure of the recovery unit 300 through the discharge line 130. The recirculation of haemorrhagic fluid in the recirculation line 150 through successively the filtration device 110 and the treatment pouch 140 is carried out until the target haematocrit level is reached, this haematocrit level being detected at the level of the haematocrit sensor 154.

Once the target haematocrit level has been reached and when the volume of concentrate (corresponding to treated haemorrhagic fluid) in the treatment pouch 140 is sufficient (for example greater than 100 ml), it may be envisaged to transfer this concentrate to the transfusion pouch 410 of the transfusion unit 400.

Preferably, but in a non-obligatory manner, rinsing of the recirculation line 150 and the filtration membrane 113 of the filtration device 110 is carried out. More specifically, it is envisaged to rinse the dead volume of the filtration circuit (VmCF) which corresponds to the volume of circuit comprised between the transfusion unit 400 and the treatment pouch 140 passing through the filtration device 110. In this respect, the clamps of the regulation valve 151 of the recirculation line 150 and the regulation valve 131 of the discharge line 130 are closed and the clamp of the regulation valve 191 of the dilution line 190 is opened. The peristaltic pump 160 returns to its operation in the direction of treatment to convey dilution fluid from the dilution unit 500 in the direction of the filtration device 110, this dilution fluid being injected in order to push the column of blood from the VmCF.

It is possible to provide an optical sensor placed at the level of the inlet 140a of the treatment pouch 140, which makes it possible to detect the nature of the fluid arriving at the level of the inlet 140a. If such a sensor is used, it is then possible to stop the pump 160 to stop the rinsing phase as soon as the optical sensor detects the presence of dilution fluid. Such an optical sensor makes it possible to command the stoppage of the pump 160 before washing fluid comes into the treatment pouch.

For this rinsing phase, it is desirable that the treatment pouch 140 integrates the separating device 141 which makes it possible to confine the concentrate in the treatment chamber 142, in the lower part of the treatment pouch 140 on the side of the outlet 140b of the treatment pouch 140. The other treatment chamber 141 formed by the separating device 141 in the upper part of the treatment pouch 140 on the side of the inlet 140a of the treatment pouch 140 makes it possible to recover fluid contained in the circuit and pushed by the dilution fluid in the rinsing phase.

It is to be noted that it is also possible to carry out several successive phases of concentration of the same bolus of haemorrhagic fluid to treat. This notably makes it possible to even better remove compounds undesired for autotransfusion, such as products undesirable for transfusion of heparin type. Preferably, a triple concentration is carried out for a same bolus of haemorrhagic fluid to treat.

In a preferred manner, when several successive concentrations are carried out, once the bolus of haemorrhagic fluid to treat has reached the target haematocrit level after a phase of concentration, the treated haemorrhagic fluid is again going to be diluted to eliminate impurities during a new concentration.

When transfer is desired, after the optional rinsing or directly after the phase of filtration and concentration, and/or after several phases of concentration, it is important to close the clamps of the regulation valve 152 of the recirculation line 150 and the regulation valve 191 of the dilution line 190 (if this is not already the case) and to open the clamps of the regulation valve 171 of the transfusion line 170 and the regulation valve 151 of the recirculation line 150 (if this is not already the case). The peristaltic pump 160 is then started in the direction of treatment and the concentrate is thus transferred from the treatment pouch 140 into the transfusion pouch 410 of the transfusion unit 400.

It is to be noted that the volume of concentrate present in the treatment chamber 140 could be conserved and thus not transferred immediately to the transfusion unit 400. The concentrate will then be cumulated with the concentrate resulting from a later treatment cycle, that is to say with another bolus.

Once the concentrate has been all or in part transferred to the transfusion unit 400, the treatment cycle is ended and another treatment cycle may be triggered with another bolus of haemorrhagic fluid.

Step E3 of transfusion of the treated haemorrhagic fluid to the patient may be carried out by disconnecting notably the transfusion pouch 410 from the treatment system, and by connecting it to the patient. If a transfusion is not necessary immediately, the transfusion pouch 410 may also be stored, a new transfusion pouch 410 being connected to the treatment system, in order to be able to recover the haemorrhagic fluid newly treated.

D. Phase of Cleaning the Filtration Device

During membrane filtration, a drop in filtration flow is generally observed throughout the process, during successive treatment cycles. This decline in the filtering capacity of the filtration membrane is due to several phenomena, notably to adsorption and to obstruction and clogging of the pores by the compounds to filter. Fouling by adsorption may represent permeability losses that can go up to 90%, or even up to total blockage of the filtration.

The proposed treatment system, in particular the particular treatment unit 100 proposed in the present document, makes it possible to clean the filtration device 110 during the treatment of a haemorrhagic fluid for a same patient, without having to dismantle said filtration device 110 from the treatment unit 100 and thus to have an overall treatment of haemorrhagic fluid undergoing no or few interruptions.

Several types of cleaning of the filtration device 110 may be envisaged with the proposed treatment system, these types of cleaning being able to be carried out alone or as a complement to each other.

The first type of cleaning consists in rinsing the intake chamber 111 of the filtration device 110 which is carried out by introducing dilution fluid from the dilution unit 500 in the direction of the inlet 111a of the intake chamber 111 of the filtration device 110. This type of rinsing has already been described above in the final phase of the treatment cycle, before the actual transfer of concentrate.

The second type of cleaning consists in rinsing the discharge chamber 112 of the filtration device 110 which is carried out by introducing dilution fluid from the dilution unit 500 in the direction of the inlet 112a of the discharge chamber 112 of the filtration device 110. This rinsing makes it possible to empty the discharge chamber 112 of filtrate which could still be present and to remove it to the recovery pouch 310 via the discharge line 130. To do so, it is possible to close the clamps of the regulation valve 171 of the transfusion line 170 and the regulation valve 151 of the recirculation line 150, and to open the clamps of the regulation valve 191 of the dilution line 190 and the regulation valve 181 of the cleaning line 180. It is also preferable that the clamp of the regulation valve 152 of the recirculation line 150 is closed. The peristaltic pump is then started to make dilution fluid circulate in the direction of treatment of the dilution pouch 500 to the filtration device 110.

The third type of cleaning consists in unclogging the filtration membrane 113 of the filtration device 110 by creation of transmembrane counterflow, as has been mentioned above. To do so, the electrical control valve 320 is closed to stop the vacuum in the recovery unit 300 and the clamp of the regulation valve 131 of the discharge line 130 is closed. The clamps of the regulation valve 171 of the transfusion line 170, the regulation valve 151 of the recirculation line 150, and the regulation valve 152 of the recirculation line 150 are also closed, and the clamps of the regulation valve 191 of the dilution line 190 and the regulation valve 181 of the cleaning line 180 are opened. The fact that the discharge line 130 is obstructed, the pressure of cleaning fluid in the discharge chamber 112 increases and thus removes the compounds that are fixed to the filtration membrane 113. It is possible to control the pressure in this discharge chamber 112 by varying the drive speed of the pump 160 or by varying the flow passing at the level of the regulation valve 181 of the cleaning line 180. Once the compounds have been unstuck from the filtration membrane 113, rinsing of the discharge chamber 112 may be carried out as previously, by opening the clamp of the regulation valve 131 of the discharge line 130. It is to be noted that the unclogging flow rate, that is to say the flow rate of circulation of cleaning fluid to create transmembrane counterflow, is preferably at least equal to the treatment flow rate, that is to say the flow rate of circulation of the haemorrhagic fluid in the treatment unit 100. It has indeed been observed that this makes it possible to have faster overall treatment times while reducing the loss of red blood cells at each cycle. The loss of red blood cells is for example only 5% compared to 10% when the unclogging flow rate passes from 1200 ml/min to 600 ml/min. The performance of the cleaning of the fibre is also improved.

The three types of cleaning described above may be carried out alone or in combination, one after the other.

For example, the following sequence of cleaning in two steps may be envisaged:

a1. unclogging the filtration membrane 113 of the filtration device 110 according to the third type of cleaning above, notably for cleaning the filtration membrane from the outside to the inside; then b1. rinsing the intake chamber 111 of the filtration device 110 according to the first type of cleaning above.

According to another example, the following sequence of cleaning in three steps may be envisaged:

a1. rinsing the intake chamber 111 of the filtration device 110 according to the first type of cleaning above; then b2. unclogging the filtration membrane 113 of the filtration device 110 according to the third type of cleaning above, notably to clean the filtration membrane from outside to inside; then c2. rinsing the intake chamber 111 of the filtration device 110 according to the first type of cleaning above.

Once the filtration device 110 has been cleaned, it is possible to adjust the dilution volume present in the treatment chamber 140, this dilution volume being able to be used for a later treatment cycle as explained above with reference to the phase for preparing the treatment cycle. Thus, after a cleaning phase, it is important to close the clamp of the regulation valve 181 of the cleaning line 180 while maintaining closed the clamp of the regulation valve 131 of the discharge line 130, and the clamp of the regulation valve 152 of the recirculation line 150 is opened while continuing to make dilution fluid circulate with the pump 160.

BIBLIOGRAPHIC REFERENCE

U.S. Pat. No. 4,886,487

The invention claimed is:

1. A treatment system for treating hemorrhagic fluid previously taken from a patient for the purpose of autotransfusion, comprising a treatment unit for treating hemorrhagic fluid, the treatment unit comprising:

a filtration device comprising a filtration membrane for tangential filtration arranged in a housing so as to separate an intake chamber from a discharge chamber, the intake chamber and the discharge chamber each having an inlet and an outlet for fluids;

a treatment pouch having an inlet and an outlet fluidically connected by a recirculation line to the outlet and to the inlet of the intake chamber of the filtration device, respectively, allowing hemorrhagic fluid to circulate in the recirculation line in a direction going from the outlet of the treatment pouch to the inlet of the treatment pouch through the intake chamber of the filtration device;

an intake line fluidically connected to the recirculation line between the outlet of the treatment pouch and the inlet of the intake chamber of the filtration device making it possible to supply the treatment unit with hemorrhagic fluid taken for the purpose of filtration through the filtration membrane of the filtration device in order to remove from the hemorrhagic fluid a filtrate comprising compounds undesired for autotransfusion;

a transfusion line fluidically connected to the recirculation line between the outlet of the treatment pouch and the inlet of the intake chamber of the filtration device making it possible to recover treated hemorrhagic fluid contained in the treatment pouch;

a discharge line fluidically connected to the outlet of the discharge chamber of the filtration device so as to discharge the filtrate having passed through the filtration membrane from the intake chamber;

wherein the treatment unit further comprises
a first flow regulation member arranged to regulate the flow in the recirculation line at the outlet of the treatment pouch, and
a dilution line intended to convey dilution fluid into the treatment unit, the dilution line being fluidically connected to the recirculation line at a position between the outlet of the treatment pouch and the inlet of the intake chamber of the filtration device.

2. The treatment system of claim 1, wherein an optical sensor is arranged at the level of the inlet of the treatment pouch to detect the nature of the fluid arriving at the level of the inlet.

3. The treatment system of claim 1, wherein the treatment pouch comprises a separating device being able to be actuated to separate the treatment pouch into a first treatment chamber on the side of the inlet of the treatment pouch and a second treatment chamber on the side of the outlet of the treatment pouch.

4. The treatment system of claim 1, wherein the treatment unit comprises a second flow regulation member arranged to regulate the flow in the dilution line, and a third flow regulation member arranged to regulate the flow in the recirculation line at the inlet of the intake chamber of the filtration device.

5. The treatment system of claim 1, wherein the treatment pouch has a substantially parallelepiped shape with the inlet and the outlet on either side of the treatment pouch along a diagonal, the treatment pouch further having an inner cavity having a tapering shape on the side of the outlet.

6. The treatment system of claim 1, wherein the filtration membrane of the filtration device is a filtration membrane with hollow fibers, the hollow fibers forming the filtration membrane extending longitudinally in the housing.

7. The treatment system of claim 6, wherein the filtration membrane with hollow fibers of the filtration device comprises hollow fibers formed from a mixture of polyester sulfone and polyvinyl pyrrolidone.

8. The treatment system of claim 1, wherein the filtration membrane of the filtration device has an overall porosity comprised between 0.1 μm and 1 μm.

9. The treatment system of claim 1, wherein the filtration membrane of the filtration device has an overall filtration surface area comprised between 0.1 m² and 1 m².

10. The treatment system of claim 1, comprising at least one peristaltic pump arranged so as to make the hemorrhagic fluid circulate in the recirculation line in a direction going from the outlet of the treatment pouch to the inlet of the treatment pouch through the intake chamber of the filtration device.

11. The treatment system of claim 1, comprising a plurality of regulation valves, each regulation valve being respectively intended to cooperate with one of the regulation members in order to regulate the corresponding flow.

12. The treatment system of claim 1, wherein the treatment unit comprises a template enabling fixation of the intake line, the discharge line, the recirculation line, the dilution line, and the transfusion line.

13. The treatment system of claim 12, comprising a support unit, the template of the treatment unit having a mistake-proofing shape making it possible to couple the treatment unit to the support unit according to a unique positioning.

14. The treatment system of claim 13, wherein the support unit forms a horizontal support plane, the filtration device of the treatment unit being intended to be coupled to the support unit such that the hollow fibers of the filtration membrane extend along a direction not comprised in the horizontal support plane.

15. The treatment system of claim 1, comprising a transfusion unit, the transfusion unit comprising a transfusion pouch having an inlet intended to be connected to the transfusion line in order to collect treated hemorrhagic fluid coming from the treatment pouch before transfusion to the patient.

16. The treatment system of claim 1, comprising a recovery unit for recovering the filtrate, the recovery unit comprising a recovery pouch having an inlet intended to be fluidically connected to the discharge line, said recovery pouch being further intended to be coupled to a device for depressurising the recovery pouch so as to make the filtrate circulate from the discharge chamber of the filtration device to the recovery pouch through the discharge line.

17. The treatment system of claim 1, comprising a recovery unit for recovering the filtrate, the recovery unit comprising a recovery pouch having an inlet intended to be fluidically connected to the discharge line, the recovery pouch being further arranged with respect to the filtration device of the treatment unit to create a vacuum pressure in the recovery pouch with respect to the filtration device so as to make the filtrate circulate from the discharge chamber of the filtration device to the recovery pouch through the discharge line.

18. The treatment system of claim 1, comprising a collection unit for collecting hemorrhagic fluid comprising a collection receptacle for collecting hemorrhagic fluid previously taken from the patient, the collection receptacle having an outlet fluidically connected to the intake line.

19. The treatment system of claim 18, further comprising an additional prefiltration device positioned in the intake line.

20. A method for using the treatment system of claim 1 for treating hemorrhagic fluid previously taken from a patient for the purpose of later autotransfusion, characterised in that, after partial or total treatment of the hemorrhagic fluid with the filtration device, a dilution fluid is injected from the dilution line into the circulation line in order to pass through the filtration device.

21. The method of claim 20, wherein cleaning of the filtration membrane is carried out by rinsing, the rinsing being carried out by obstructing the outlet of the treatment pouch at the level of the first flow regulation member, by obstructing the discharge line at the level of the outlet of the discharge chamber of the filtration device, and by injecting cleaning fluid into the intake chamber from the dilution line.

22. The method of claim 21, wherein rinsing is stopped as soon as the optical sensor detects the presence of the dilution fluid.

23. The method of claim 21, wherein, before rinsing, the separating device is controlled to isolate the treated hemorrhagic fluid in the second treatment chamber.

24. The method of claim 21, wherein a dilution of the hemorrhagic fluid contained in the treatment system is carried out, the dilution being performed by obstructing the outlet of the treatment pouch at the level of the first flow regulation member, then by injecting cleaning fluid into the intake chamber from the dilution line, then by isolating the treated hemorrhagic fluid present in the treatment pouch when the fluid present in the circulation line has a hematocrit level below a threshold value.

25. The treatment system of claim 1, wherein the filtration membrane of the filtration device has an overall porosity of 0.6 μm.

26. The treatment system of claim 1, wherein the filtration membrane of the filtration device has an overall filtration surface area comprised between 0.2 m$^2$ and 0.6 m$^2$.

27. The treatment system of claim 18, wherein the collection receptacle integrates a prefiltration device making it possible to carry out a prefiltration of the hemorrhagic fluid before being transmitted into the treatment unit.

* * * * *